US011033375B2

(12) United States Patent
St. Germain

(10) Patent No.: US 11,033,375 B2
(45) Date of Patent: Jun. 15, 2021

(54) DEVICES AND METHODS FOR SPHINCTER REINFORCEMENT

(71) Applicant: Jon St. Germain, Elk River, MN (US)

(72) Inventor: Jon St. Germain, Elk River, MN (US)

(73) Assignee: Innomedex LLC, Elk River, MN (US)

( * ) Notice: Subject to any disclaimer, the term of this patent is extended or adjusted under 35 U.S.C. 154(b) by 55 days.

(21) Appl. No.: 15/883,044

(22) Filed: Jan. 29, 2018

(65) Prior Publication Data

US 2018/0344444 A1    Dec. 6, 2018

Related U.S. Application Data

(60) Provisional application No. 62/451,756, filed on Jan. 29, 2017.

(51) Int. Cl.
*A61F 2/00* (2006.01)
*A61F 2/04* (2013.01)
*A61M 25/00* (2006.01)
*A61M 25/01* (2006.01)
*A61B 17/34* (2006.01)
*A61B 17/30* (2006.01)

(52) U.S. Cl.
CPC .............. *A61F 2/0036* (2013.01); *A61F 2/04* (2013.01); *A61M 25/003* (2013.01); *A61B 17/3468* (2013.01); *A61B 17/3478* (2013.01); *A61B 2017/306* (2013.01); *A61F 2002/044* (2013.01); *A61F 2002/047* (2013.01); *A61F 2210/009* (2013.01); *A61F 2210/0014* (2013.01); *A61F 2220/0033* (2013.01); *A61F 2230/0004* (2013.01); *A61F 2230/0008* (2013.01); *A61F 2230/0013* (2013.01); *A61F 2230/0019* (2013.01); *A61F 2230/0034* (2013.01); *A61F 2230/0065* (2013.01); *A61F 2230/0069* (2013.01); *A61F 2230/0091* (2013.01); *A61F 2250/0067* (2013.01); *A61M 25/007* (2013.01); *A61M 2025/018* (2013.01)

(58) Field of Classification Search
CPC .......... A61F 2002/044; A61F 2002/047; A61F 2210/0014; A61F 2210/009; A61F 2230/0008; A61F 2230/0065; A61F 2230/0069; A61F 2/0036; A61F 2/04
See application file for complete search history.

(56) References Cited

U.S. PATENT DOCUMENTS 2,668,547 A    2/1954  Wille
4,055,861 A   11/1977  Carpentier et al.
4,164,046 A    8/1979  Cooley
(Continued)

FOREIGN PATENT DOCUMENTS

CN    203169363 U    9/2013
FR        394944       2/1909

*Primary Examiner* — Christine H Matthews
(74) *Attorney, Agent, or Firm* — Jinn Su

(57) ABSTRACT

Sphincter reinforcement devices are described. Sphincter reinforcement devices may be configured to be placed at least partially around a bodily passage at or near a sphincter. In one embodiment, a sphincter reinforcement device may comprise a ring including a tubular structure. The ring may be expandable. The tubular structure may be hollow. The tubular structure may have a first end and a second end. The first end may be configured to be coupled to the second end. The tubular structure may include a braided material.

12 Claims, 31 Drawing Sheets

(56) References Cited

U.S. PATENT DOCUMENTS

| | | |
|---|---|---|
| 4,204,282 A | 5/1980 | Bolt |
| 4,556,050 A | 12/1985 | Hodgson et al. |
| 4,571,749 A | 2/1986 | Fischell |
| 4,584,990 A | 4/1986 | Haber et al. |
| 4,587,954 A | 5/1986 | Haber |
| 4,796,603 A | 1/1989 | Dahlke et al. |
| 4,878,889 A | 11/1989 | Polyak |
| 4,994,020 A | 2/1991 | Polyak |
| 5,006,106 A | 4/1991 | Angelchik |
| 5,104,407 A | 4/1992 | Lam et al. |
| 6,432,040 B1 | 8/2002 | Meah |
| 6,572,627 B2 | 6/2003 | Gabbay |
| 6,749,556 B2 | 6/2004 | Banik |
| 6,997,952 B2 | 2/2006 | Furukawa et al. |
| 7,087,088 B2 | 8/2006 | Berg et al. |
| 7,201,757 B2 | 4/2007 | Knudson et al. |
| 7,695,427 B2 | 4/2010 | Kugler et al. |
| 7,762,942 B2 | 7/2010 | Neisz et al. |
| 8,012,202 B2 | 9/2011 | Alameddine |
| 8,715,157 B2 | 5/2014 | Berg et al. |
| 8,864,823 B2 | 10/2014 | Cartledge et al. |
| 9,192,472 B2 | 11/2015 | Gross et al. |
| 9,402,704 B2 | 8/2016 | Frigstad et al. |
| 9,427,296 B2 | 8/2016 | Griguol |
| 2004/0133219 A1 | 7/2004 | Forsell |
| 2005/0125014 A1 | 6/2005 | Dulucq et al. |
| 2005/0283041 A1* | 12/2005 | Egle .................. A61F 5/0056 600/37 |
| 2005/0288776 A1* | 12/2005 | Shaoulian ............ A61F 2/2448 623/2.37 |
| 2006/0276812 A1 | 12/2006 | Hill et al. |
| 2009/0192346 A1 | 7/2009 | Rosenblatt |
| 2011/0066231 A1 | 3/2011 | Cartledge et al. |
| 2011/0066254 A1 | 3/2011 | Forsell |
| 2014/0243588 A1* | 8/2014 | Kirchhoff .............. A61F 5/445 600/37 |
| 2015/0105859 A1 | 4/2015 | Frigstad et al. |
| 2016/0166417 A1* | 6/2016 | Nihalani ............... A61F 5/0066 600/37 |
| 2016/0193062 A1 | 7/2016 | Lesti et al. |
| 2017/0100249 A1 | 4/2017 | Miller et al. |

\* cited by examiner

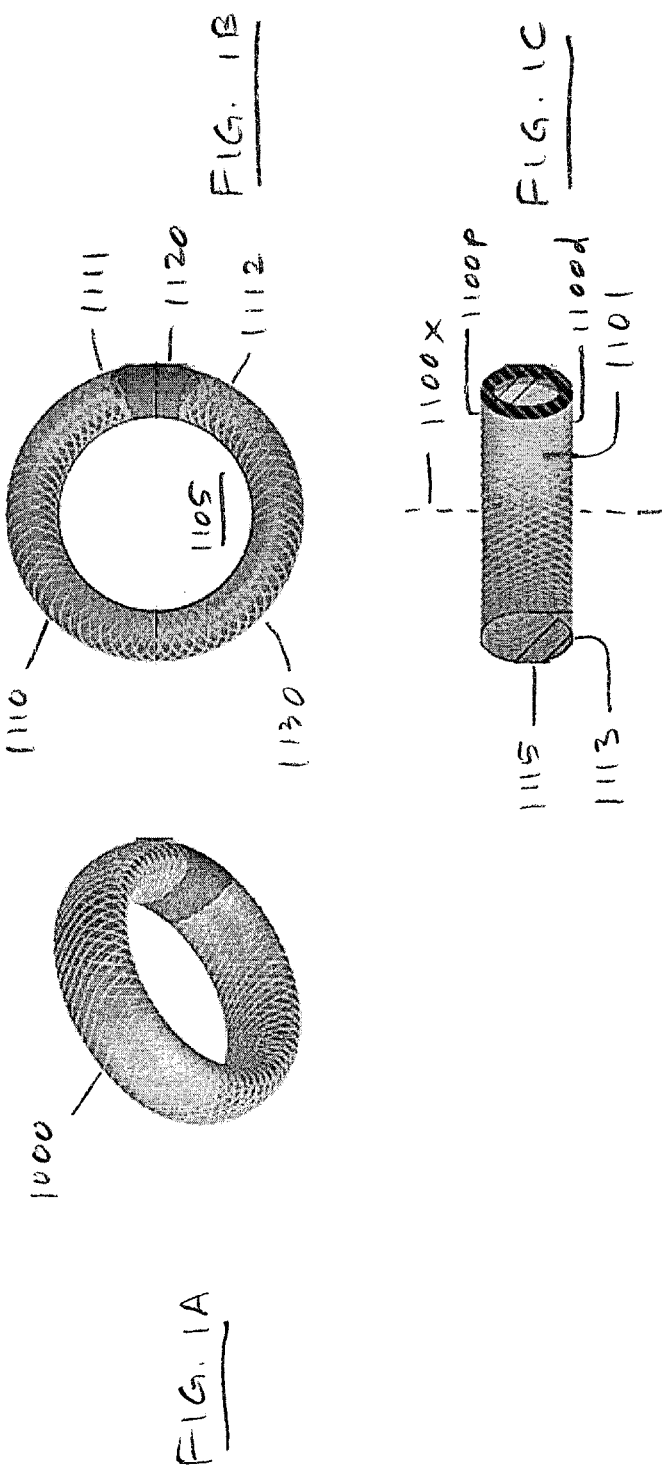

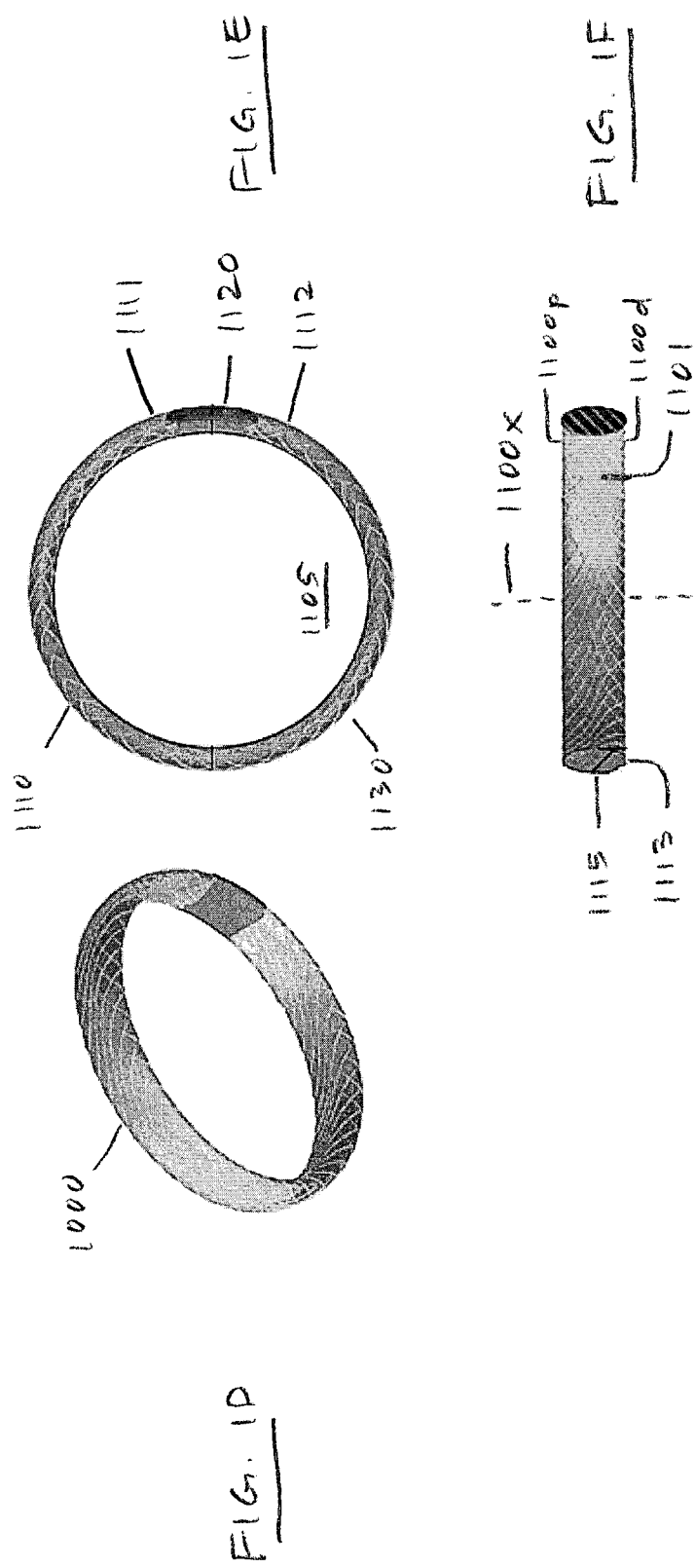

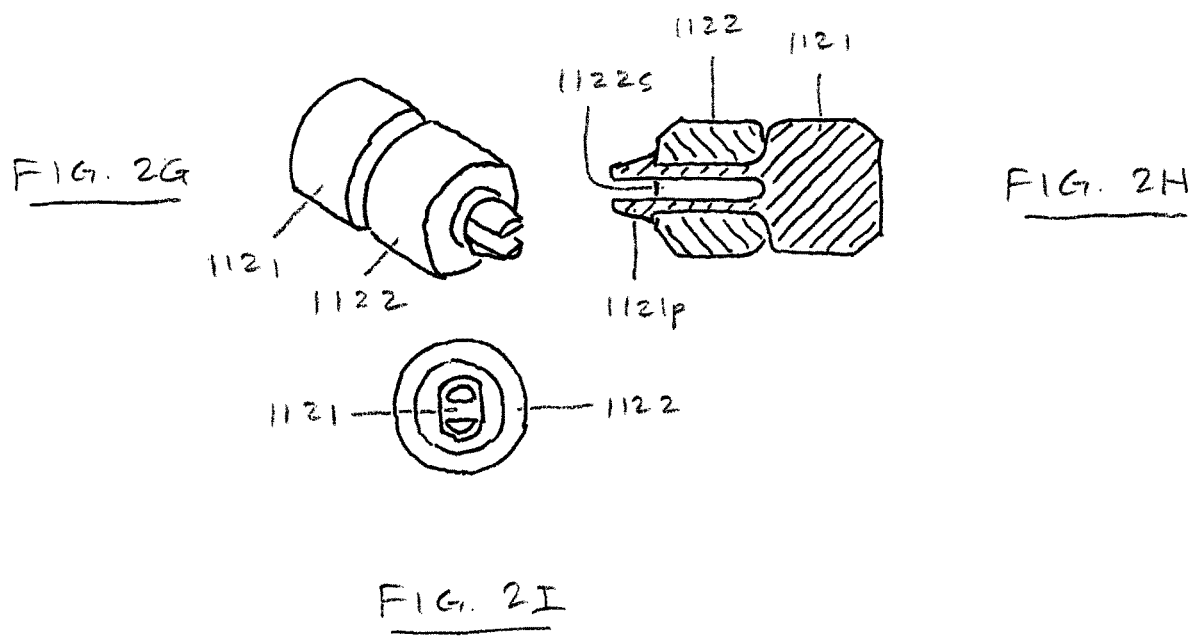

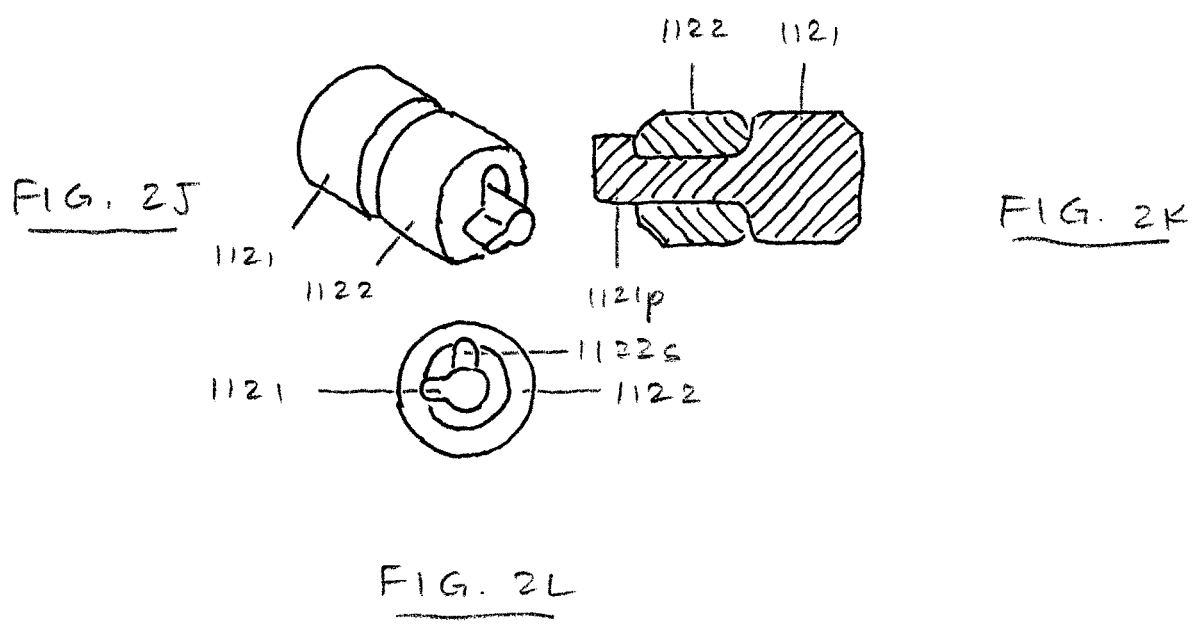

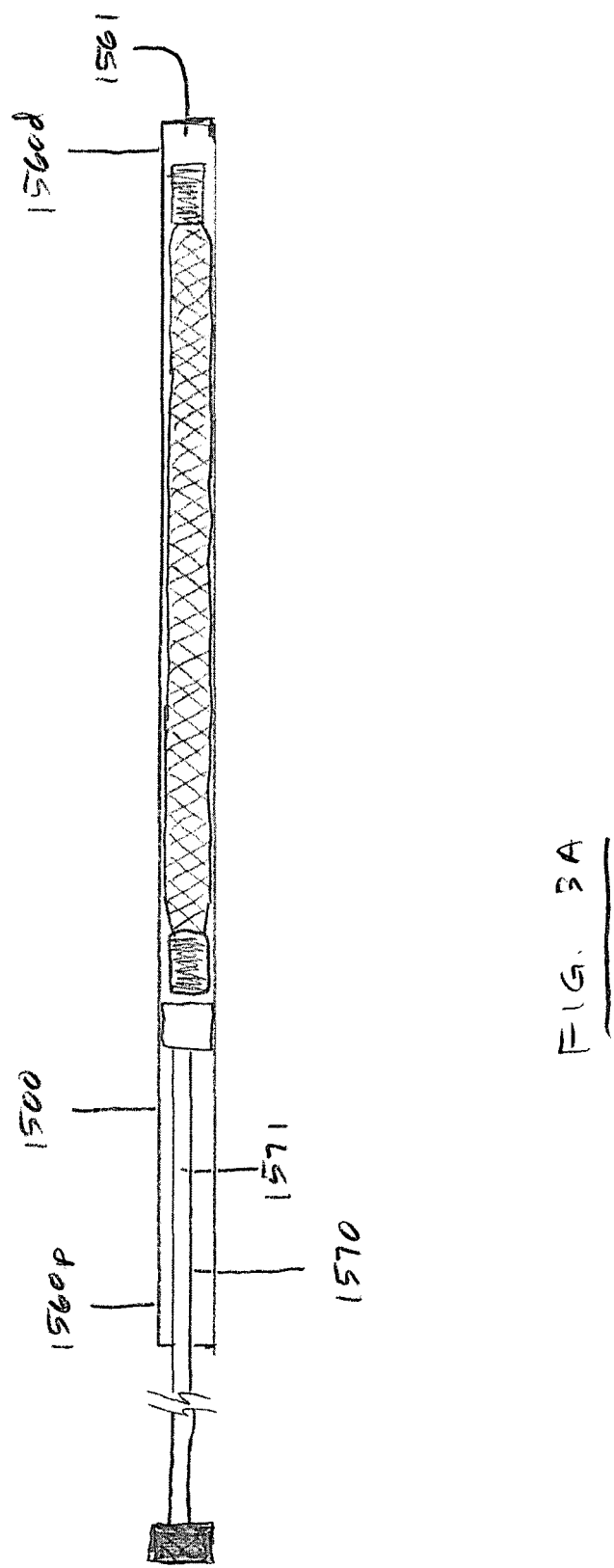

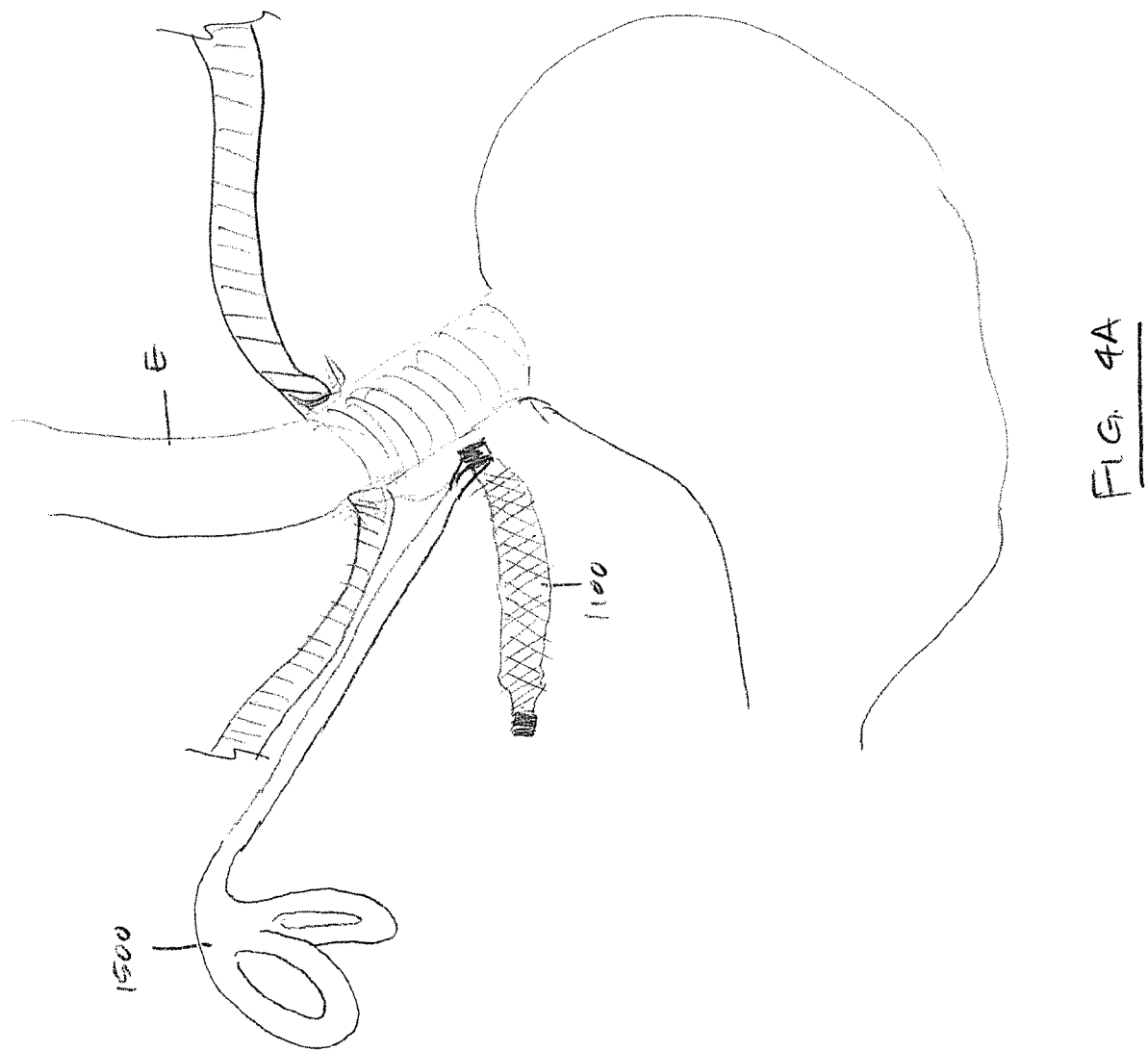

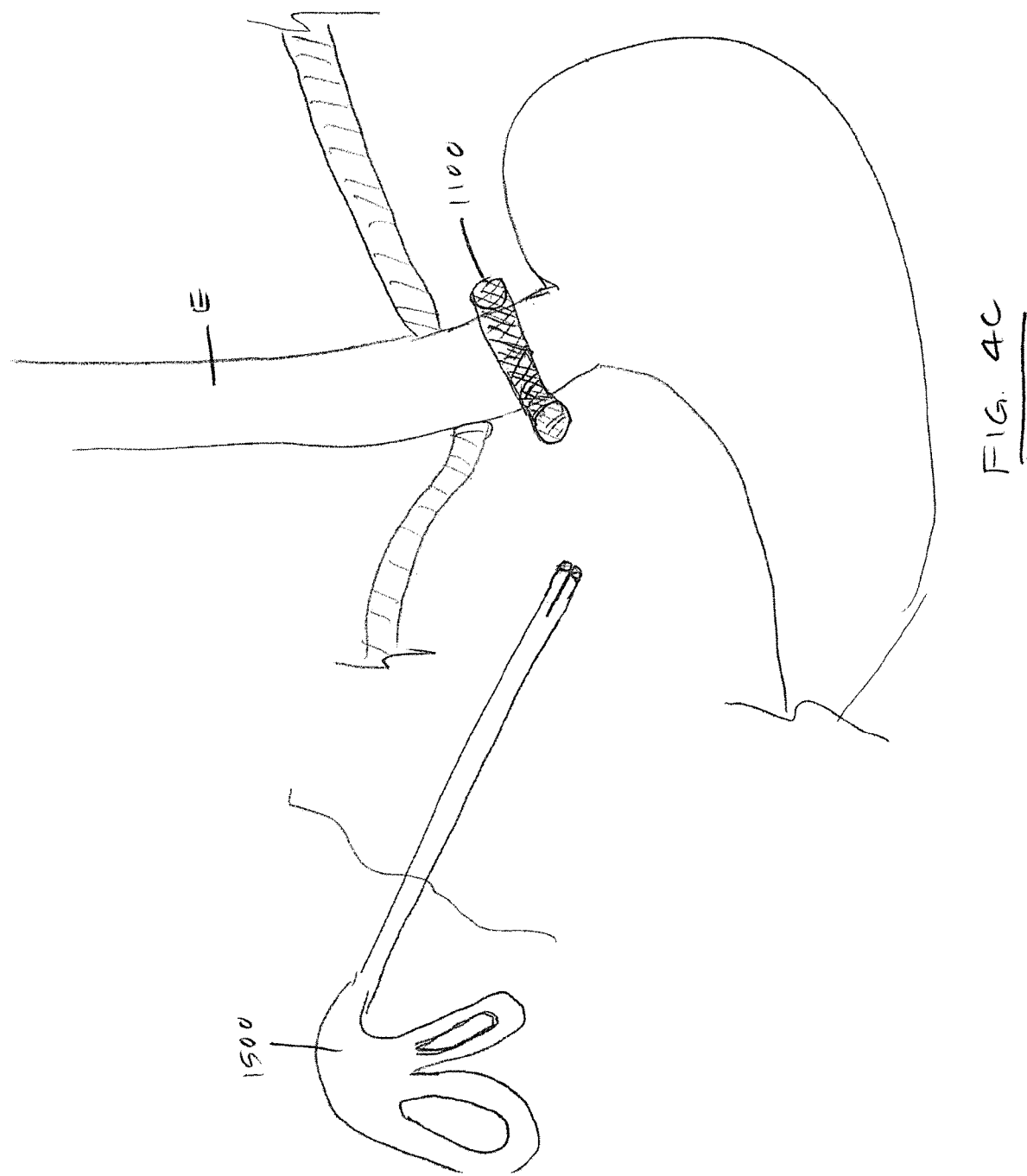

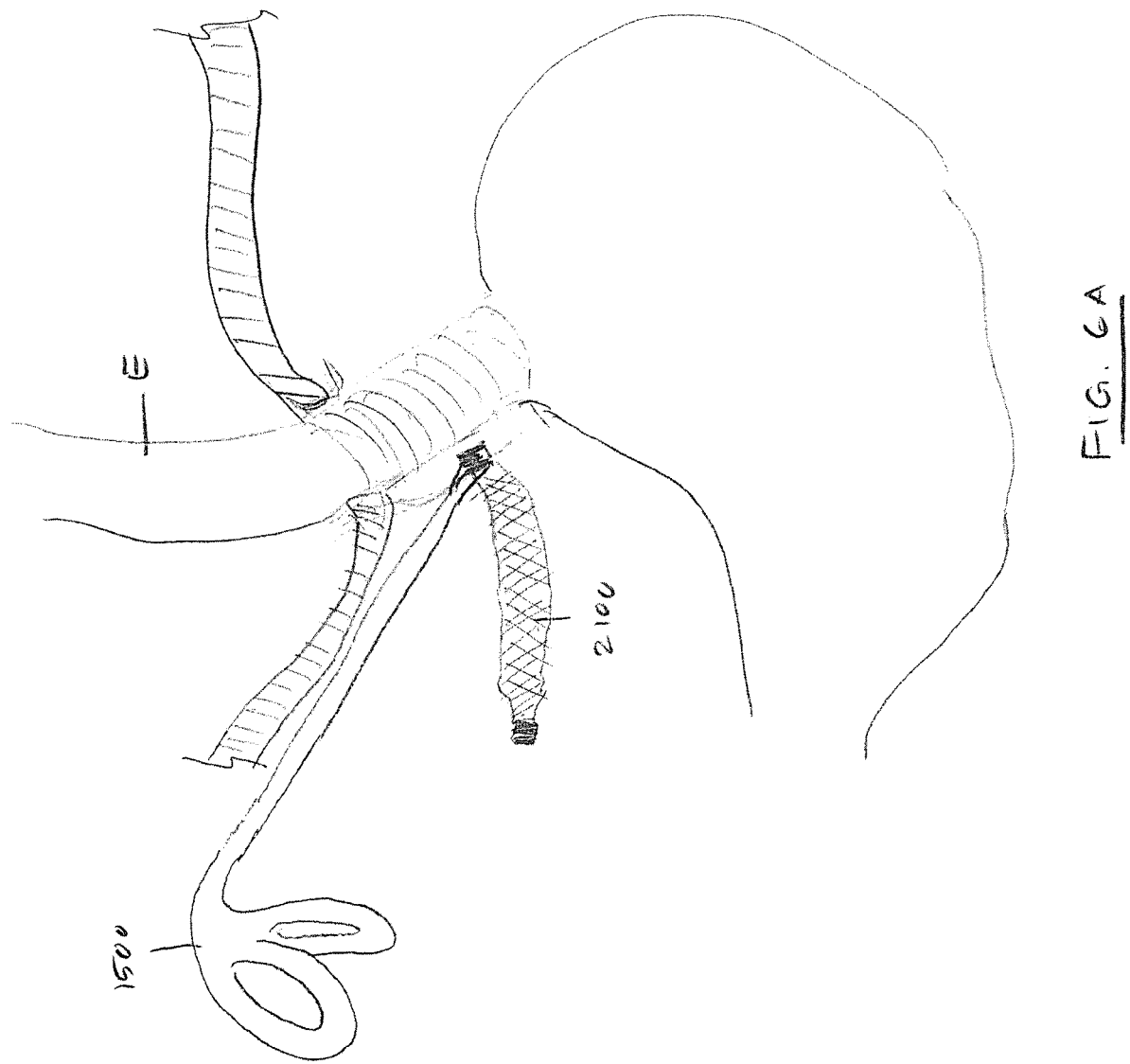

DEVICES AND METHODS FOR SPHINCTER REINFORCEMENT

CROSS-REFERENCE TO RELATED APPLICATION

This application claims the benefit of U.S. provisional application No. 62/451,756, filed Jan. 29, 2017, which is hereby incorporated by reference in its entirety.

BACKGROUND

Defective sphincters of the body lead to a number of prevalent disorders. As examples, a defective lower esophageal sphincter leads to gastroesophageal reflux disease (GERD), a defective anal sphincter leads to fecal incontinence, a defective urinary sphincter leads to urinary incontinence, and a defective pyloric sphincter leads to bile reflux. Defective sphincters occur when the natural-state muscle tone of a sphincter muscle is compromised, resulting in a reduced ability to properly regulate flow through lumen of a bodily passage.

SUMMARY

Sphincter reinforcement devices are described. Sphincter reinforcement devices may be configured to be placed at least partially around a bodily passage at or near a sphincter. In one embodiment, a sphincter reinforcement device may comprise a ring including a tubular structure. The ring may be expandable. The tubular structure may be hollow. The tubular structure may have a first end and a second end. The first end may be configured to be coupled to the second end. The tubular structure may include a braided material.

BRIEF DESCRIPTION OF THE DRAWINGS

FIGS. 1A-1F show one embodiment of a sphincter reinforcement device 1000.

FIGS. 3A-3B show two embodiments of a delivery device 1500.

FIGS. 4A-4D show one embodiment of a method for reinforcing a lower esophageal sphincter with ring 1100.

FIG. 5 shows one embodiment of a sphincter reinforcement device 2000.

DESCRIPTION

Figure 1H:
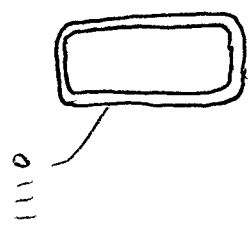
FIG. 1G-1I show various cross sections for tubular structure 1110.

Sphincter reinforcement devices are described. Sphincter reinforcement devices may help a sphincter to close after material has passed through the sphincter. Sphincter reinforcement devices may be placed at least partially around a bodily passage such as an esophagus, rectum, urethra, intestine, or other bodily passage. Sphincter reinforcement devices may be placed at or near a sphincter, such as a lower esophageal sphincter (LES), internal anal sphincter, urinary sphincter, pyloric sphincter, or other sphincter.

Sphincter reinforcement devices may be resilient. Sphincter reinforcement devices may expand and/or lengthen to allow a sphincter to open and allow material to pass through the sphincter. When expanded or lengthened, sphincter reinforcement devices may exert an inward force to help the sphincter close after the material has passed through the sphincter.

FIGS. 1A-1F show one embodiment of a sphincter reinforcement device 1000. FIGS. 1A-1C show perspective, top, and side cross-sectional views of ring 1100 unexpanded. FIGS. 1D-1F show perspective, top, and side cross-sectional views of ring 1100 expanded.

Sphincter reinforcement device 1000 may include a ring 1100. Ring 1100 may have a proximal portion 1100p and a distal portion 1100d. Ring 1100 may have an inward surface 1101. Ring 1100 may have a longitudinal axis 1100x which passes through its center or opening. Ring 1100 may define a ring lumen 1105 at its center or opening.

Ring lumen 1105 may have a shape that is circular or oval. Ring lumen 1105 may have a shape that is asymmetrical, such as triangular or D-shaped. Ring lumen 1105 may have a shape that is similar to an outside of a bodily passage around which ring 1100 is placed.

Ring lumen 1105 may have an unexpanded size that is approximately the same size or slightly smaller than an outside of an unexpanded bodily passage around which ring 1100 is placed. In one embodiment, ring lumen 1105 may have an unexpanded size that is approximately 0 mm to 3 mm smaller than an outside of an unexpanded bodily passage around which ring 1100 is placed. This sizing may reduce or prevent tissue erosion on the outside of the bodily passage by ring 1100. Ring 1100 may apply little or no pressure on an unexpanded bodily passage. Ring lumen 1105 may have an expanded size that is large enough to allow the bodily passage to expand without affecting normal function.

In one embodiment, a ring 1100 used to reinforce a lower esophageal sphincter may have a ring lumen 1105 with an unexpanded width of approximately 12 mm, and be capable of expanding up to approximately 20 mm. In another embodiment, a ring 1100 used to reinforce an internal anal sphincter may have a ring lumen 1105 with an unexpanded width of approximately 20 mm, and be capable of expanding up to approximately 35 mm.

Ring 1100 may have a contact length that depends on a length of inward surface 1101 between proximal portion 1100p and distal portion 1100d that contacts an outside of a bodily passage when the bodily passage expands. In one embodiment, a ring 1100 used to reinforce a lower esophageal sphincter may have a contact length of approximately 5 mm to 15 mm. The contact length may also depend on a curvature of inward surface 1101. A contact length that is longer may allow for a lower contact pressure by inward surface 1101 against an outside of a bodily passage.

Ring 1100 may include a tubular structure 1110. Tubular structure 1110 may include a first end 1111, a second end 1112, and a wall 1113. Tubular structure 1110 may be hollow, with wall 1113 defining a tubular structure lumen 1115.

Tubular structure 1110 may be initially straight and then bent or curved to into the shape of ring 1100. Tubular structure 1110 may have at least a portion that is bent or curved. Tubular structure 1110 may bent or curved by either elastic deformation or plastic deformation. Tubular structure 1110 may be bent or curved either temporarily or permanently.

Tubular structure 1110 may have a cross section that is oval or elliptical. The longest axis of the oval, or the major axis of the ellipse, may be oriented parallel or substantially parallel to longitudinal axis 1100x, or to an outside surface of the bodily passage. The shortest axis of the oval, or the minor axis of the ellipse, may be oriented perpendicular or substantially perpendicular to longitudinal axis 1100x, or to an outside surface of the bodily passage. This orientation of the longest axis or major axis may increase the contact length of inward surface 1101. In one embodiment, tubular structure 1110 may have a longest axis or major axis of approximately 10 mm to 20 mm, and a shortest axis or minor axis of approximately 5 mm to 10 mm.

Figure 1I:
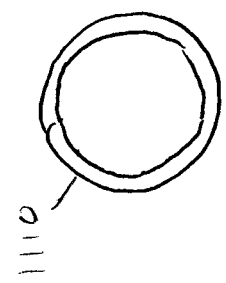
Figure 1G:
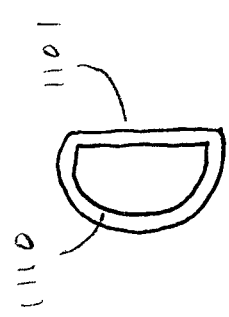

Tubular structure 1110 may have a cross section that is D-shaped, as shown in FIG. 1G. The flat part of the "D" may be positioned along inward surface 1101 of ring 1100. This positioning may increase the contact length of inward surface 1101. Tubular structure 1110 may have a cross section that is circular, as shown in FIG. 1H, rectangular with rounded corners, as shown in FIG. 1I, or other suitable shape.

Tubular structure 1110 may have a cross section that is not uniform. Tubular structure 1110 may have a cross section that changes in size and/or shape along its length. As an example, a ring 1100 used to reinforce a lower esophageal sphincter may have a tubular structure 1110 with a cross section that is circular on an anterior of the esophagus and oval along a posterior of the esophagus. As another example, a ring 1100 used to reinforce a lower esophageal sphincter may have a tubular structure 1110 with a cross section that is oval along an anterior of the esophagus and more oval, or flattened, along a posterior of the esophagus.

Tubular structure 1110 may be at least partially made of a woven or braided material. The weave or braid may be at least partially made of one or more of metal, plastic, or other suitable material. The weave or braid may be at least partially made of one or more of nitinol, stainless steel, PEEK, polypropylene, or other suitable material.

Tubular structure 1110 may have a braid angle, braid density, filament diameter, filament size, and number of filaments selected to give a desired combination of compliance, resilience, porosity, and tubular strength that seeks to match the characteristics of a native sphincter to provide improved competency. In one embodiment, the weave or braid may have a braid angle of approximately 55 to 85 degrees. The weave or braid may have a braid density of approximately 70 to 100 crossings per inch. The filament diameter may be approximately 0.001 in. to 0.005 in. The number of filaments may be approximately 16 to 96.

Figure 2A:
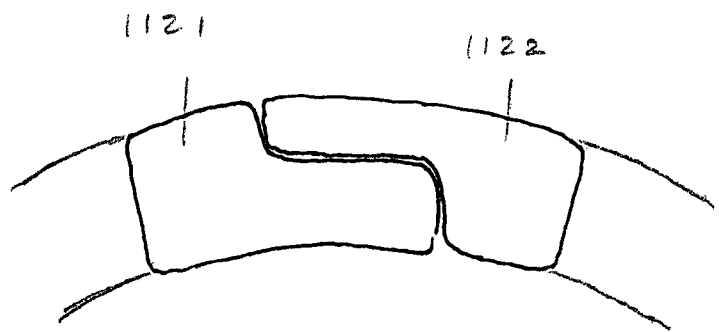
FIGS. 2A-2O show various embodiments of connectors 1120.
Figure 2B:
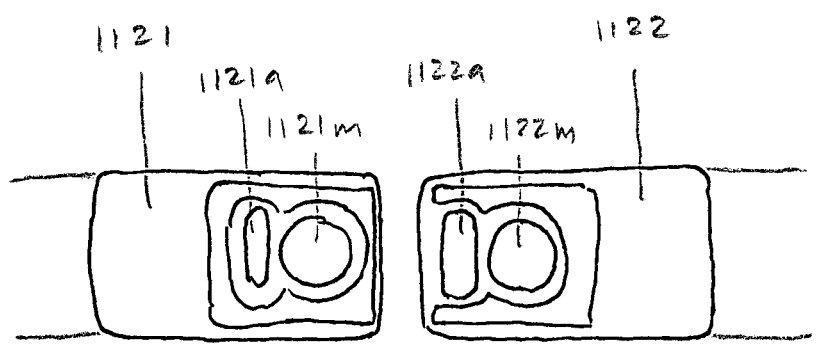
Figure 2C:
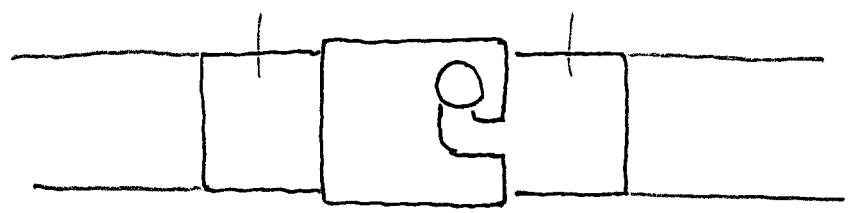
Figure 2D:
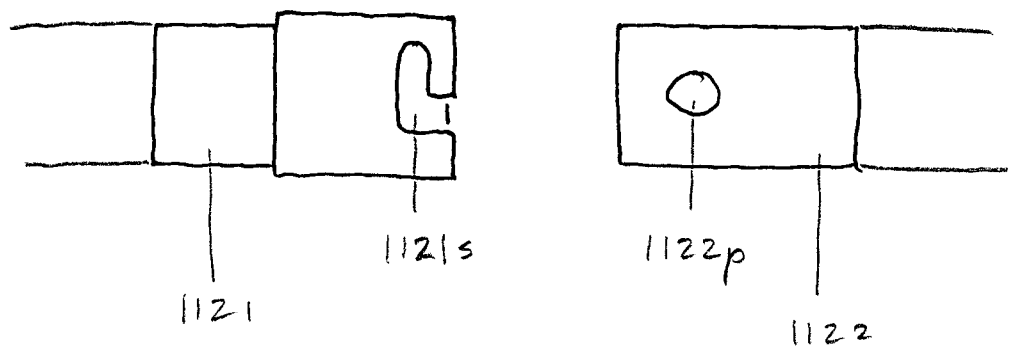
Figure 2E:
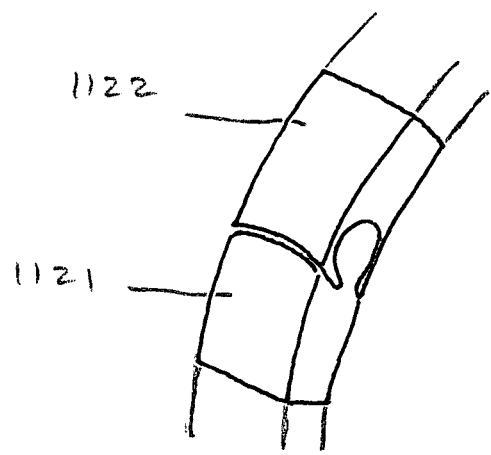
Figure 2F:
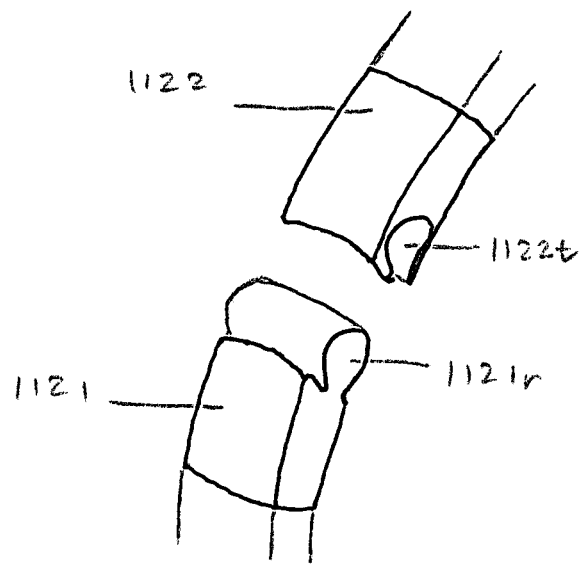
Figures 2M, 2N, 2O:
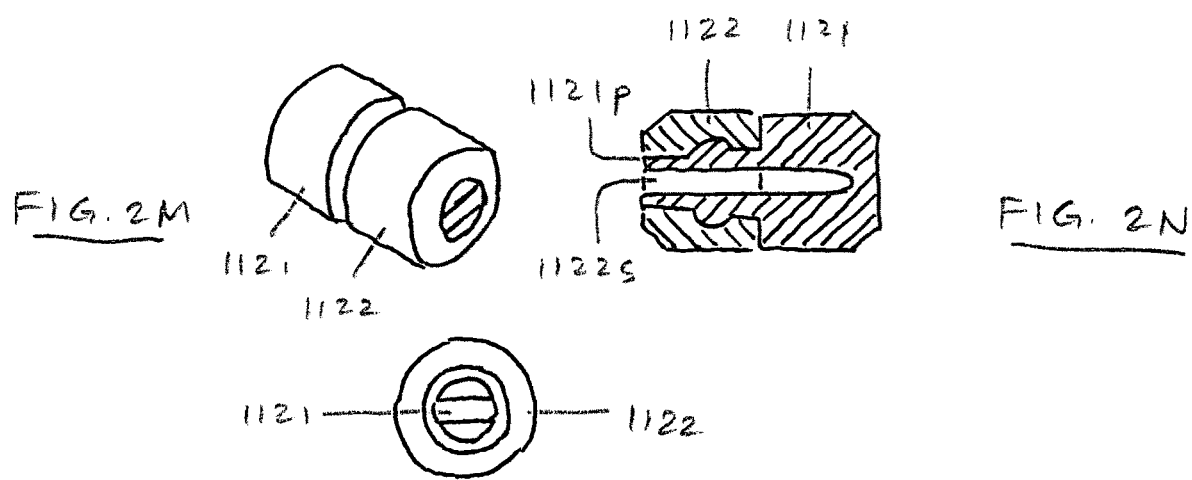

FIGS. 2A-2O show various embodiments of connectors 1120.

Ring 1100 may include one or more connectors 1120. Connectors 1120 may include a first connector 1121 and a second connector 1122 coupled to first end 1111 and/or second end 1112 of tubular structure 1110, respectively. First connector 1121 may be configured to detachably or non-detachably couple to second connector 1122. Connectors 1120 may include one or more of a mechanical clip, buckle-like mechanism, interference fit connector, magnet, or other suitable connectors. Connectors 1120 may include one or more sutures. Connectors 1120 may be hollow to allow access to tubular structure lumen 1115. Connectors 1120 may include one or more grasping features, such as grasping tabs and/or suture loops, which allow connectors 1120 to be more easily handled by graspers.

FIGS. 2A-2B show coupled and detached views of one embodiment of first connector 1121 and second connector 1122. First connector 1121 may include a magnet and/or a ferromagnetic material 1121m configured to be coupled to a magnet and/or a ferromagnetic material 1122m of second connector 1122. First connector 1121 may also include a tab 1121a configured to fit into a slot 1122a of second connector 1122.

FIGS. 2C-2D show coupled and detached views of another embodiment of first connector 1121 and second connector 1122. First connector 1121 may include a male bayonet connector with a slot 1121s configured to be coupled to a female bayonet connector with a pin 1122p of second connector 1122.

FIGS. 2E-2F shows another embodiment of first connector 1121 and second connector 1122. First connector 1121 may include a rail 1121r configured to slide into a track 1122t of second connector 1122.

FIG. 2G-2I show perspective, cross-section, and end views of another embodiment of first connector 1121 and second connector 1122. First connector 1121 may include a pin 1121p configured to be inserted into and retained by a socket 1122s of second connector 1122.

FIG. 2J-2L show perspective, cross-section, and end views of another embodiment of first connector 1121 and second connector 1122. First connector 1121 may include a keyed pin 1121p configured to be inserted into and rotated in a keyhole socket 1122s of second connector 1122.

FIG. 2M-2O show cross-section and end views of another embodiment of first connector 1121 and second connector 1122. First connector 1121 may include a pin 1121p configured to be inserted into and retained by a socket 1122s of second connector 1122.

Ring 1100 may include a covering 1130. Covering 1130 may be coupled to tubular structure 1110 and/or connectors 1120. Covering 1130 may be discrete or formed integrally with tubular structure 1110 and/or one or more connectors 1120. Covering 1130 may at least partially cover tubular structure 1110. Covering 1130 may be flexible and/or resilient. Covering 1130 may be made of ePTFE, silicone, urethane, or other suitable material. In one embodiment, covering 1130 may have a thickness of approximately 10 microns to 30 microns.

Covering 1130 may distribute forces of tubular structure 1110 in contact with adjacent tissue. Covering 1130 may reduce or prevent tissue erosion on the outside of the bodily passage by tubular structure 1110. Covering 1130 may discourage tissue ingrowth into tubular structure 1110. Covering 1130 may be configured to not substantially alter the expansion properties of ring 1100. Covering 1130 may have properties that are accounted for in the expansion properties of ring 1100.

Alternatively, ring 1100 may have no covering. Tubular structure 1110 may be at least partially made of a woven or braided material with a weave or braid that is sufficiently dense to prevent tissue ingrowth. Tubular structure 1110 may be made of a woven or braided material with a weave or braid that has interstices that are small enough to prevent tissue ingrowth.

Tubular structure 1110 and/or covering 1130 may be coated with an agent or drug. Tubular structure 1110 and/or covering 1130 may release the agent or drug over time. The agent or drug may include an antibiotic to reduce the likelihood of infection.

Ring 1100 may be resiliently expandable. Ring 1100 may have an unexpanded state and, after expanding, return to the unexpanded state.

Ring 1100 may be asymmetrically expandable. Ring 1100 may expand along a portion of tubular structure 1110 to accommodate non-centered passage of material through a bodily passage and ring lumen 1105.

Tubular structure 1110 may be flexible. Tubular structure 1110 may be compliant. Tubular structure 1110 may give or flex at an area of wall 1113 where force is applied. Tubular structure 1110 may give or flex at an area of wall 1113 to accommodate non-centered passage of material through a bodily passage and ring lumen 1105. Wall 1113 may give or flex into tubular structure lumen 1115. Tubular structure 1110 may be sufficiently rigid to maintain tubular structure lumen 1115.

Ring 1100 occupies a volume when implanted in tissue. This volume may provide at least part of a space needed when ring 1100 and ring lumen 1105 expand. Tubular structure 1110 may have a cross section with a size that becomes smaller as ring lumen 1105 expands. Tubular structure 1110 may flatten in a direction of expansion, such as perpendicular to longitudinal axis 1100$x$, as ring lumen 1105 expands. The space created by the reduction in cross section and/or flattening of tubular structure 1110 may reduce the amount of surrounding tissue moved and/or compressed when ring 1100 and ring lumen 1105 expand.

Ring 1100 may exert little or no inward force when unexpanded. Ring 1100 may exert an inward force when expanded. Ring 1100 may be configured to exert an inward force that is not so large as to significantly inhibit the sphincter from opening and/or expanding when material passes through the sphincter. Ring 1100 may be configured to exert an inward force that is sufficiently large to help a sphincter at least partially close and/or return to an unexpanded size after the material has passed through the sphincter.

Ring 1100 may exert an inward force that increases, remains constant, or decreases as ring 1100 expands. Ring 1100 may be configured with a desired amount of inward force, depending on how much closure assist is needed.

In one embodiment, a ring 1100 used to reinforce a lower esophageal sphincter may exert an inward force at a pressure of approximately 5 mmHg to 15 mmHg. In another embodiment, a ring 1100 used to reinforce an internal anal sphincter may exert an inward force at a pressure of approximately 5 mmHg to 50 mmHg.

FIG. 3A shows one embodiment of a delivery device 1500.

Delivery device 1500 may include a delivery sheath 1560. Delivery sheath 1560 may include a proximal portion 1560$p$ and a distal portion 1560$d$. Delivery sheath 1560 may include a sheath lumen 1561.

Delivery device 1500 may include a plunger 1570. Plunger 1570 may be slidably disposed within sheath lumen 1561. Plunger 1570 may define a plunger lumen 1571.

Figure 3B:
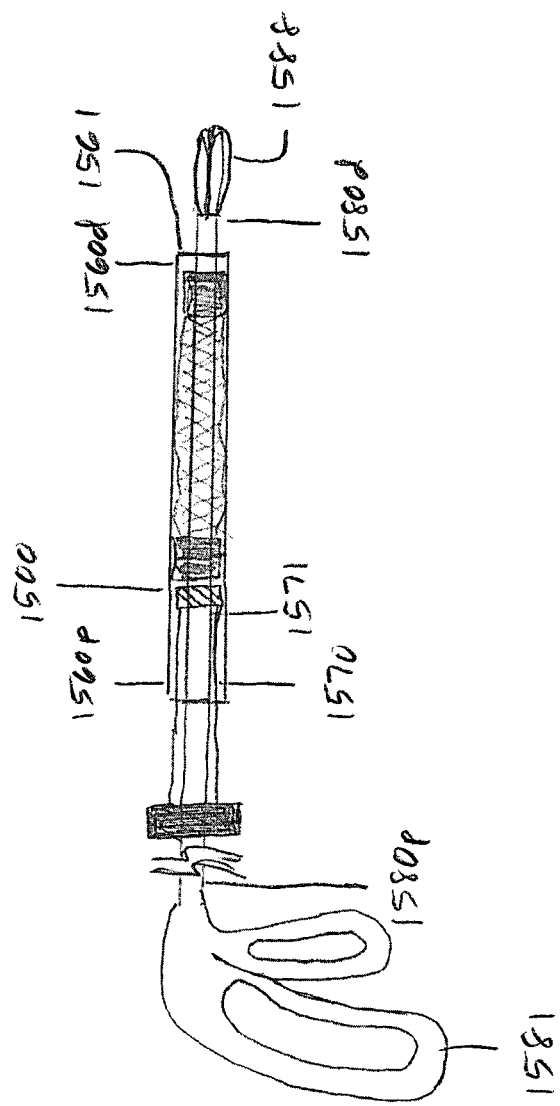

FIG. 3B shows another embodiment of a delivery device 1500.

Delivery device 1500 may include a grasper 1580. Grasper 1580 may include a proximal portion 1580$p$ and a distal portion 1580$d$. Grasper 1580 may include a handle 1581 at proximal portion 1580$p$, and grasper jaws 1588 at distal portion 1580$d$. Grasper 1580 may pass through plunger lumen 1571, tubular structure lumen 1115, and connectors 1120.

FIGS. 4A-4D show one embodiment of a method for reinforcing a lower esophageal sphincter with ring 1100.

FIG. 4A shows introducing ring 1100 into the abdominal cavity. The abdominal cavity may be accessed using a four-port, single-port, or other suitable laparoscopic system. A tunnel may be created at least partially around the esophagus E at the placement site. The placement site may be approximately 10 mm above to 10 mm below the lower esophageal sphincter. The tunnel may be created through surgical dissection. The posterior vagus nerve may be excluded during dissection.

Ring 1100 may be available in various sizes or in a single, universal size. For ring 1100 available in various sizes, a distance around an outside of the esophagus E may be measured, and a ring 1100 of suitable size may be selected based on the distance. A ring 1100 of suitable inward force may also be selected based on the amount of closure assist desired.

Tubular structure 1110 may be lengthened to reduce its cross section. Tubular structure 1110 may be constrained in a reduced cross section in delivery sheath 1560 of delivery device 1500.

Delivery sheath 1560 with ring 1100 may be inserted into the abdominal cavity. Delivery sheath 1560 with ring 1100 may be placed in or near the tunnel created around the esophagus E. Delivery sheath 1560 may be pulled back over plunger 1570 to release ring 1100 from sheath lumen 1561. Alternatively, plunger 1570 may be advanced through delivery sheath 1560 to release ring 1100 from sheath lumen 1561. Tubular structure 1110 may return to an unconstrained cross section. Alternatively, ring 1100 may be introduced into the abdominal cavity without delivery device 1500.

Figure 4B:
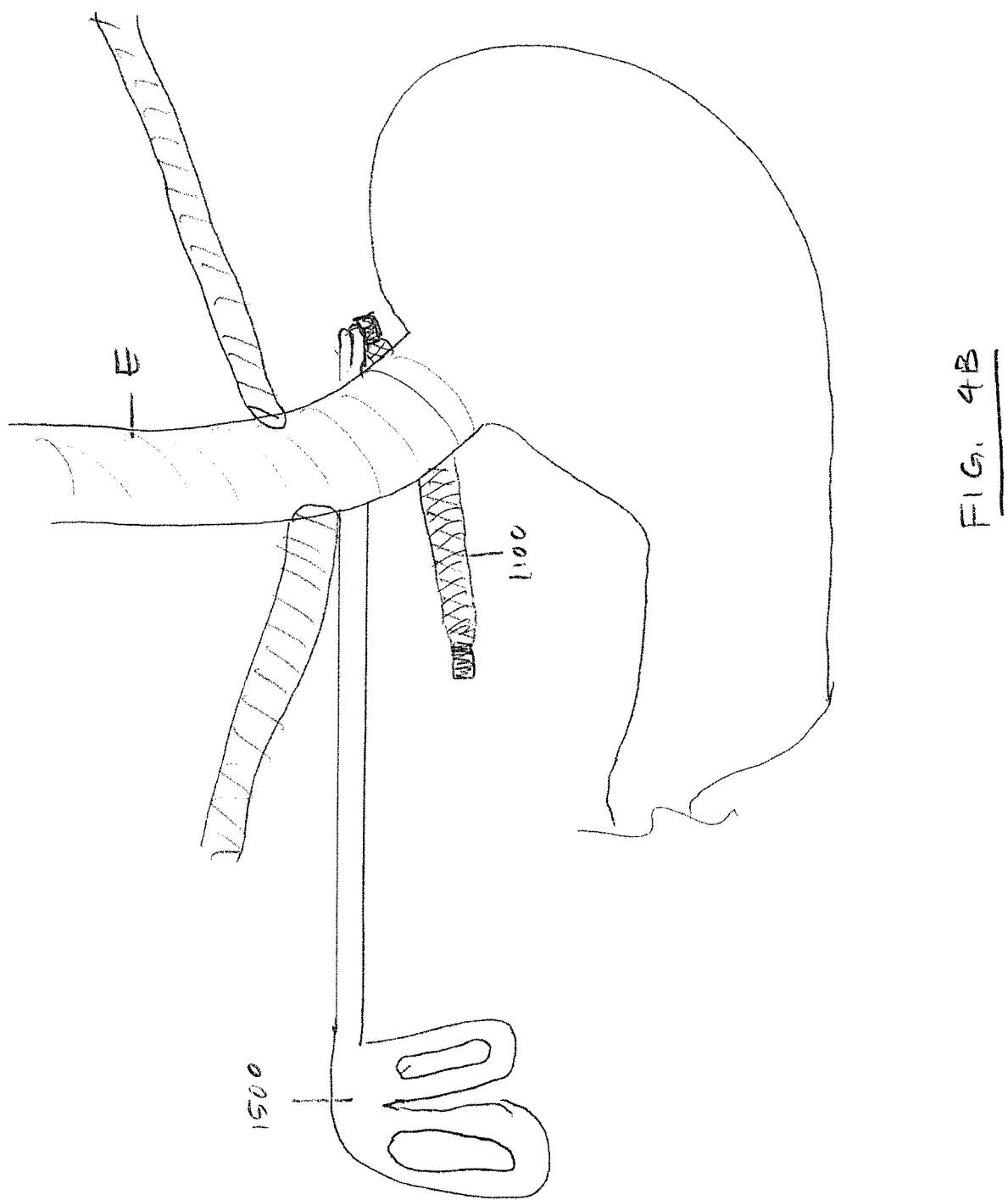

FIG. 4B shows placing ring 1100 around the esophagus E. Ring 1100 may be maneuvered and/or adjusted using a grasper and/or other tools.

Figure 4D:
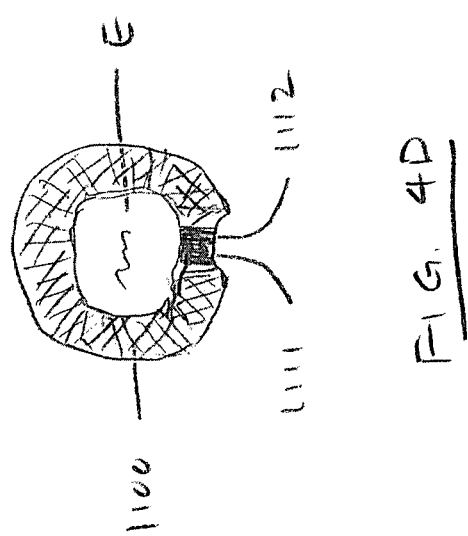

FIGS. 4C-4D show front and top views of ring 1100 placed around the esophagus E. First end 1111 may be detachably or non-detachably coupled to second end 1112. Alternatively, first end 1111 and second 1112 may be left uncoupled to each other.

Ring 1100 may be removed by dissecting tissue surrounding ring 1100, uncoupling first end 1111 from second end 1112 or cutting ring 1100, and pulling on one end of tubular structure 1110 to reduce a cross section of tubular structure 1110 and remove ring 1100 from around the esophagus E.

FIG. 5 shows one embodiment of a sphincter reinforcement device 2000.

Sphincter reinforcement device 2000 may include a spiral 2100. Spiral 2100 may have a proximal portion 2100$p$ and a distal portion 2100$d$. Spiral 2100 may have an inward surface 2101. Spiral 2100 may have a longitudinal axis 2100$x$ which passes through its center or opening. Spiral 2100 may define a spiral lumen 2105 at its center or opening.

Spiral lumen 2105 may have a shape that is circular or oval. Spiral lumen 2105 may have a shape that is asymmetrical, such as triangular or D-shaped. Spiral lumen 2105 may have a shape that is similar to an outside of a bodily passage around which spiral 2100 is placed.

Spiral lumen 2105 may have an unexpanded size that is approximately the same size or slightly smaller than an outside of an unexpanded bodily passage around which spiral 2100 is placed. In one embodiment, spiral lumen 2105 may have an unexpanded size that is approximately 0 mm to 5 mm smaller than an outside of an unexpanded bodily passage around which spiral 2100 is placed. This sizing may reduce or prevent tissue erosion on the outside of the bodily passage by spiral 2100. Spiral 2100 may apply little or no pressure on an unexpanded bodily passage. Spiral lumen 2105 may have an expanded size that is large enough to allow the bodily passage to expand without affecting normal function.

In one embodiment, a spiral 2100 used to reinforce a lower esophageal sphincter may have a spiral lumen 2105 with an unexpanded width of approximately 12 mm, and be capable of expanding up to approximately 20 mm. In another embodiment, a spiral 2100 used to reinforce an internal anal sphincter may have a spiral lumen 2105 with an unexpanded width of approximately 20 mm, and be capable of expanding up to approximately 35 mm.

Spiral 2100 may have a total contact length that depends on a total length of inward surface 2101 between proximal portion 2100p and distal portion 2100d that contacts an outside of a bodily passage when the bodily passage expands. Spiral 2100 may have a total contact length that depends a contact length of a single turn of spiral 2100, and a number of turns of spiral 2100. In one embodiment, a spiral 2100 used to reinforce a lower esophageal sphincter may have a total contact length of approximately 5 mm to 20 mm. The total contact length may also depend on a curvature of inward surface 2101. A total contact length that is longer may allow for a lower contact pressure by inward surface 2101 against an outside of a bodily passage.

Spiral 2100 may include a tubular structure 2110. Tubular structure 2110 may include a first end 2111, a second end 2112, and a wall 2113. Tubular structure 2110 may be hollow, with wall 2113 defining a tubular structure lumen 2115.

Spiral 2100 may include one or more turns or coils of tubular structure 2110.

Tubular structure 2110 may have a cross section that is oval or elliptical. The longest axis of the oval, or the major axis of the ellipse, may be oriented parallel or substantially parallel to longitudinal axis 2100x, or to an outside surface of the bodily passage. The shortest axis of the oval, or the minor axis of the ellipse, may be oriented perpendicular or substantially perpendicular to longitudinal axis 2100x, or to an outside surface of the bodily passage. This orientation of the longest axis or major axis may increase the contact length of inward surface 2101. In one embodiment, tubular structure 2110 may have a longest axis or major axis of approximately 10 mm to 20 mm, and a shortest axis or minor axis of approximately 5 mm to 10 mm.

Tubular structure 2110 may have a cross section that is D-shaped. The flat part of the "D" may be positioned along inward surface 2101 of spiral 2100. This positioning may increase the contact length of inward surface 2101. Tubular structure 2110 may have a cross section that is circular, rectangular with rounded corners, or other suitable shape.

Tubular structure 2110 may have a cross section that is not uniform. Tubular structure 2110 may have a cross section that changes in size and/or shape along its length. As an example, a spiral 2100 used to reinforce a lower esophageal sphincter may have a tubular structure 2110 with a cross section that is circular on an anterior of the esophagus and oval along a posterior of the esophagus. As another example, a spiral 2100 used to reinforce a lower esophageal sphincter may have a tubular structure 2110 with a cross section that is oval along an anterior of the esophagus and more oval, or flattened, along a posterior of the esophagus.

Tubular structure 2110 may be at least partially made of a woven or braided material. The weave or braid may be at least partially made of one or more of metal, plastic, or other suitable material. The weave or braid may be at least partially made of one or more of nitinol, stainless steel, PEEK, polypropylene, or other suitable material.

Tubular structure 2110 may have a braid angle, braid density, filament diameter, filament size, and number of filaments selected to give a desired combination of compliance, resilience, porosity, and tubular strength that seeks to match the characteristics of a native sphincter to provide improved competency. In one embodiment, the weave or braid may have a braid angle of approximately 55 to 85 degrees. The weave or braid may have a braid density of approximately 70 to 100 crossings per inch. The filament diameter may be approximately 0.001 in. to 0.005 in. The number of filaments may be approximately 16 to 96.

Spiral 2100 may include a covering 2130. Covering 2130 may be coupled to tubular structure 2110. Covering 2130 may be discrete or formed integrally with tubular structure 2110. Covering 2130 may at least partially cover tubular structure 2110. Covering 2130 may be flexible and/or resilient. Covering 2130 may be made of ePTFE, silicone, urethane, or other suitable material. In one embodiment, covering 2130 may have a thickness of approximately 10 microns to 30 microns.

Covering 2130 may distribute forces of tubular structure 2110 in contact with adjacent tissue. Covering 2130 may reduce or prevent tissue erosion on the outside of the bodily passage by tubular structure 2110. Covering 2130 may discourage tissue ingrowth into tubular structure 2110. Covering 2130 may be configured to not substantially alter the expansion properties of spiral 2100. Covering 2130 may have properties that are accounted for in the expansion properties of spiral 2100.

Alternatively, spiral 2100 may have no covering. Tubular structure 2110 may be at least partially made of a woven or braided material with a weave or braid that is sufficiently dense to prevent tissue ingrowth. Tubular structure 2110 may be made of a woven or braided material with a weave or braid that has interstices that are small enough to prevent tissue ingrowth.

Tubular structure 2110 and/or covering 2130 may be coated with an agent or drug. Tubular structure 2110 and/or covering 2130 may release the agent or drug over time. The agent or drug may include an antibiotic to reduce the likelihood of infection.

Spiral 2100 may be resiliently expandable. Spiral 2100 may have an unexpanded state and, after expanding, return to the unexpanded state.

Spiral 2100 may be asymmetrically expandable. Spiral 2100 may expand along a portion of tubular structure 2110 to accommodate non-centered passage of material through a bodily passage and spiral lumen 2105.

Tubular structure 2110 may be flexible. Tubular structure 2110 may be compliant. Tubular structure 2110 may give or flex at an area of wall 2113 where force is applied. Tubular structure 2110 may give or flex at an area of wall 2113 to accommodate non-centered passage of material through a bodily passage and spiral lumen 2105. Wall 2113 may give or flex into tubular structure lumen 2115. Tubular structure 2110 may be sufficiently rigid to maintain tubular structure lumen 2115.

Spiral 2100 occupies a volume when implanted in tissue. This volume may provide at least part of a space needed when spiral 2100 and spiral lumen 2105 expand. Tubular structure 2110 may have a cross section with a size that becomes smaller as spiral lumen 2105 expands. Tubular structure 2110 may flatten in a direction of expansion, such as perpendicular to longitudinal axis 2100x, as spiral lumen 2105 expands. The space created by the reduction in cross section and/or flattening of tubular structure 2110 may reduce the amount of surrounding tissue moved and/or compressed when spiral 2100 and spiral lumen 2105 expand.

Spiral 2100 may exert little or no inward force when unexpanded. Spiral 2100 may exert an inward force when expanded. Spiral 2100 may be configured to exert an inward force that is not so large as to significantly inhibit the sphincter from opening and/or expanding when material passes through the sphincter. Spiral 2100 may be configured to exert an inward force that is sufficiently large to help a sphincter at least partially close and/or return to an unexpanded size after the material has passed through the sphincter.

Spiral 2100 may exert an inward force that increases, remains constant, or decreases as spiral 2100 expands. Spiral 2100 may be configured with a desired amount of inward force, depending on how much closure assist is needed.

In one embodiment, a spiral 2100 used to reinforce a lower esophageal sphincter may exert an inward force at a pressure of approximately 5 mmHg to 15 mmHg. In another embodiment, a spiral 2100 used to reinforce an internal anal sphincter may exert an inward force at a pressure of approximately 5 mmHg to 50 mmHg.

FIGS. 6A-6D show one embodiment of a method for reinforcing a lower esophageal sphincter with spiral 2100.

Figure 6:
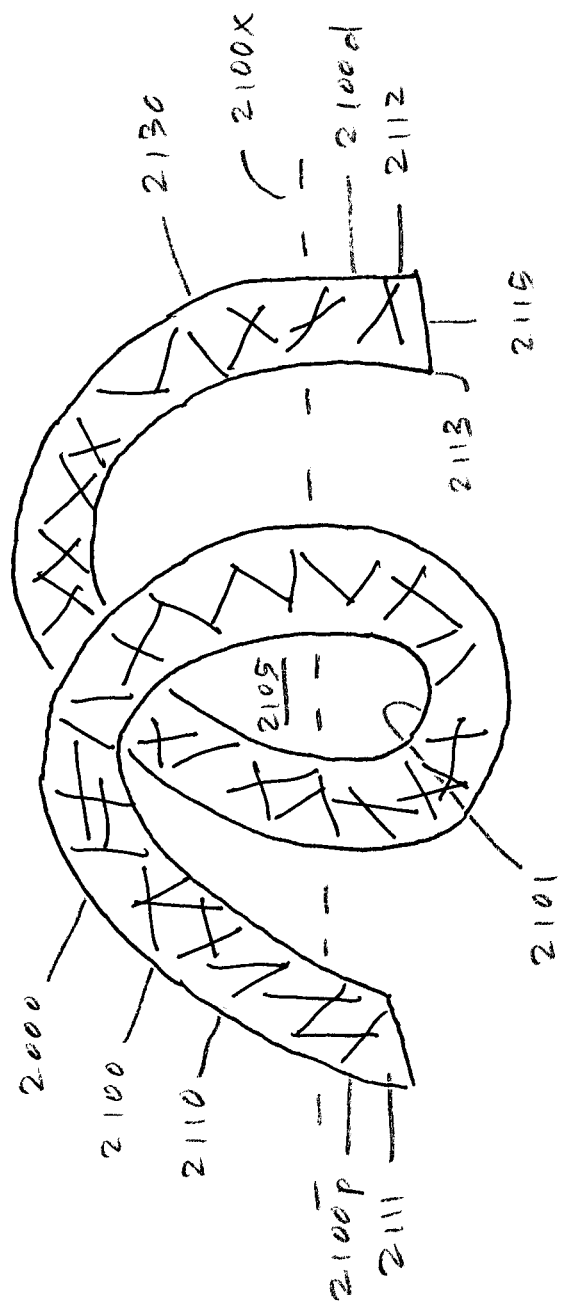
FIGS. 6A-6D show one embodiment of a method for reinforcing a lower esophageal sphincter with spiral 2100.

FIG. 6A shows introducing spiral 2100 into the abdominal cavity. The abdominal cavity may be accessed using a four-port, single-port, or other suitable laparoscopic system. A tunnel may be created at least partially around the esophagus E at the placement site. The placement site may be approximately 10 mm above to 10 mm below the lower esophageal sphincter. The tunnel may be created through surgical dissection. The posterior vagus nerve may be excluded during dissection.

Spiral 2100 may be available in various sizes or in a single, universal size. For spiral 2100 available in various sizes, a distance around an outside of the esophagus E may be measured, and a spiral 2100 of suitable size may be selected based on the distance. A spiral 2100 of suitable inward force may also be selected based on the amount of closure assist desired.

Tubular structure 2110 may be lengthened to reduce its cross section. Tubular structure 2110 may be constrained in a reduced cross section in delivery sheath 1560 of delivery device 1500.

Delivery sheath 1560 with spiral 2100 may be inserted into the abdominal cavity. Delivery sheath 1560 with spiral 2100 may be placed in or near the tunnel created around the esophagus E. Delivery sheath 1560 may be pulled back over plunger 1570 to release spiral 2100 from sheath lumen 1561. Alternatively, plunger 1570 may be advanced through delivery sheath 1560 to release spiral 2100 from sheath lumen 1561. Tubular structure 2110 may return to an unconstrained cross section. Alternatively, spiral 2100 may be introduced into the abdominal cavity without delivery device 1500.

Figure 6B:
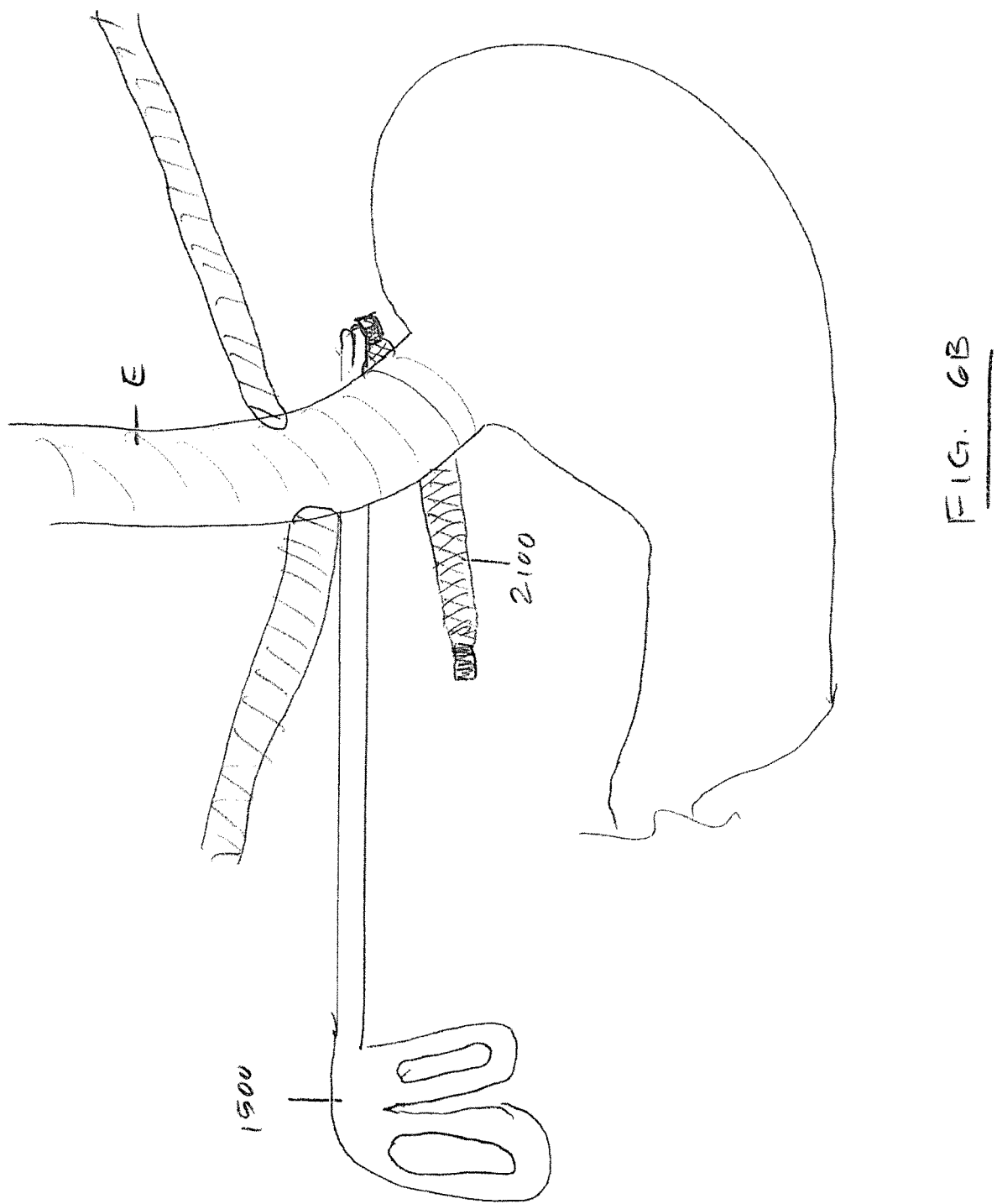

FIG. 6B shows placing spiral 2100 around the esophagus E. Spiral 2100 may be maneuvered and/or adjusted using a grasper and/or other tools.

Figure 6C:
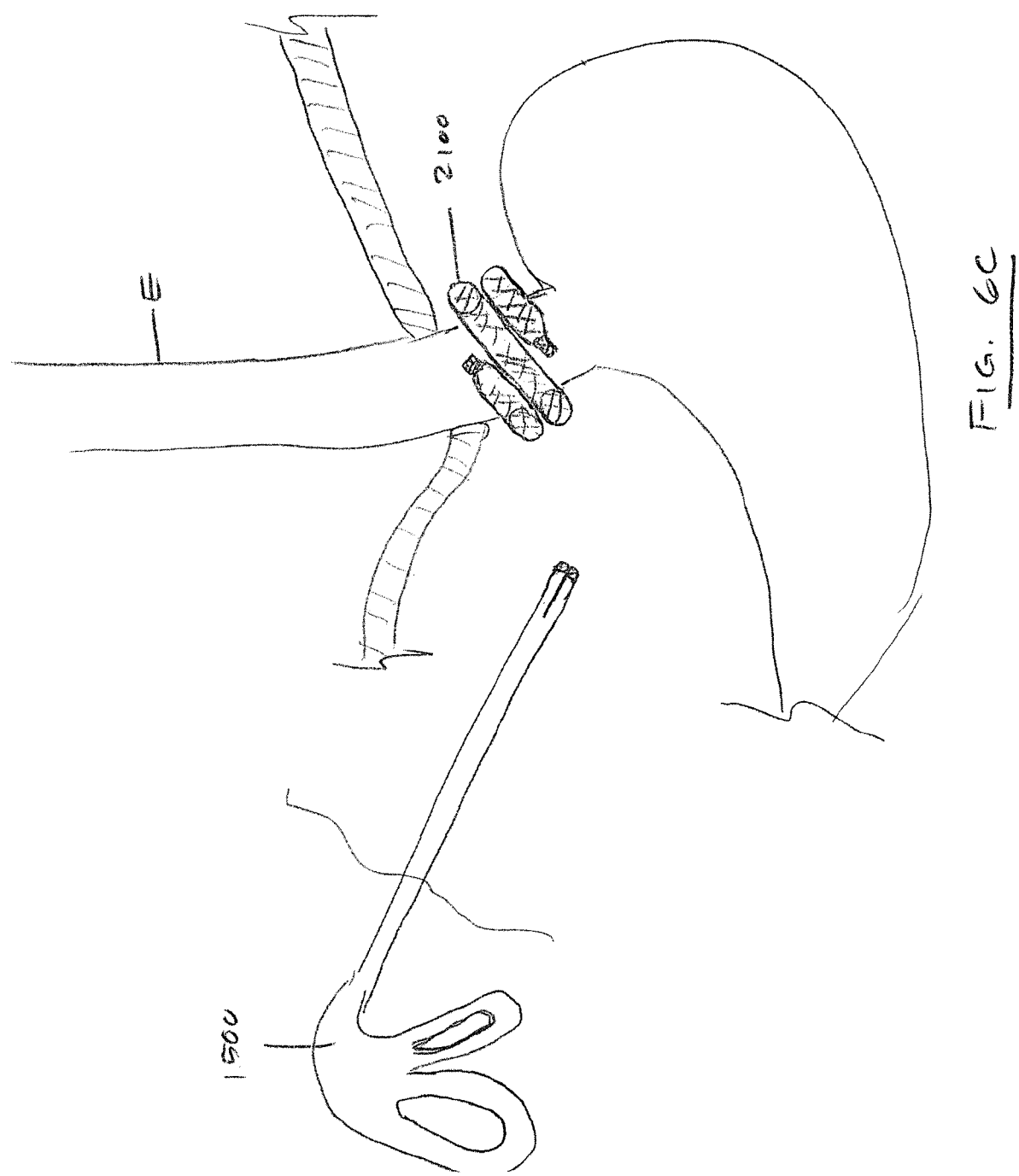
Figure 6D:
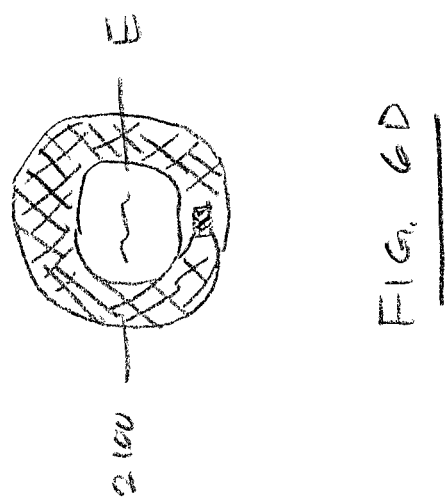

FIGS. 6C-6D show front and top views of spiral 2100 placed around the esophagus E. Spiral 2100 may wrap around the esophagus E one, one-and-a-half, or any number of times.

Spiral 2100 may be removed by dissecting tissue surrounding spiral 2100, and pulling on one end of tubular structure 2110 to reduce a cross section of tubular structure 2110 and remove spiral 2100 from around the esophagus E.

Figure 7:
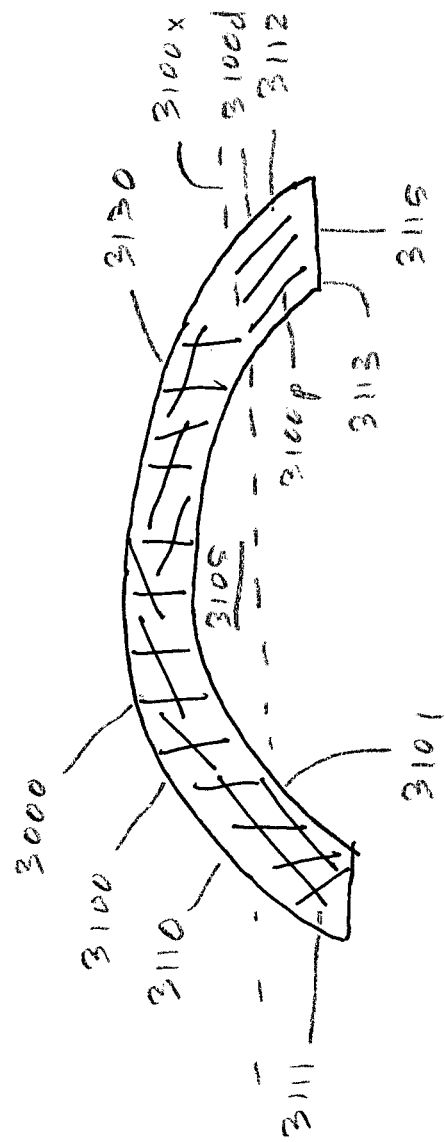
FIG. 7 shows one embodiment of sphincter reinforcement device 3000.

FIG. 7 shows one embodiment of sphincter reinforcement device 3000.

Sphincter reinforcement device 3000 may include an arcuate element 3100. Arcuate element 3100 may have a proximal portion 3100p and a distal portion 3100d. Arcuate element 3100 may have an inward surface 3101. Arcuate element 3100 may have a longitudinal axis 3100x. Arcuate element 3100 may define an arc interior 3105.

Arc interior 3105 may have a shape that is similar to an outside of a bodily passage against which arcuate element 3100 is placed.

Arc interior 3105 may have an unlengthened size that is approximately the same size or slightly smaller than an outside of an unexpanded bodily passage against which arcuate element 3100 is placed. In one embodiment, arc interior 3105 may have an unexpanded size that is approximately 0 mm to 3 mm smaller than an outside of an unexpanded bodily passage against which arcuate element 3100 is placed. This sizing may reduce or prevent tissue erosion on the outside of the bodily passage by arcuate element 3100. Arcuate element may apply little or no pressure on an unexpanded bodily passage. Arc interior 3105 may have an expanded size that is large enough to allow the bodily passage to expand without affecting normal function.

In one embodiment, an arcuate element 3100 used to reinforce a lower esophageal sphincter may have an arc interior 3105 with an unexpanded width of approximately 12 mm, and be capable of expanding up to approximately 20 mm. In another embodiment, an arcuate element 3100 used to reinforce an internal anal sphincter may have an arc interior 3105 with an unexpanded width of approximately 20 mm, and be capable of expanding up to approximately 35 mm.

Arcuate element 3100 may have a contact length that depends on a length of inward surface 3101 between proximal portion 3100p and distal portion 3100d that contacts an outside of a bodily passage when the bodily passage expands. In one embodiment, an arcuate element 3100 used to reinforce a lower esophageal sphincter may have a contact length of approximately 10 mm to 25 mm. The contact length may also depend on a curvature of inward surface 3101. A contact length that is longer may allow for a lower contact pressure by inward surface 3101 against an outside of a bodily passage.

Arcuate element 3100 may include a tubular structure 3110. Tubular structure 3110 may include a first end 3111, a second end 3112, and a wall 3113. Tubular structure 3110 may be hollow, with wall 3113 defining a tubular structure lumen 3115.

Tubular structure 3110 may have a cross section that is oval or elliptical. The longest axis of the oval, or the major axis of the ellipse, may be oriented parallel or substantially parallel to longitudinal axis 3100x, or to an outside surface of the bodily passage. The shortest axis of the oval, or the minor axis of the ellipse, may be oriented perpendicular or substantially perpendicular to longitudinal axis 3100x, or to an outside surface of the bodily passage. This orientation of the longest axis or major axis may increase the contact length of inward surface 3101. In one embodiment, tubular structure 3110 may have a longest axis or major axis of approximately 10 mm to 20 mm, and a shortest axis or minor axis of approximately 5 mm to 10 mm.

Tubular structure 3110 may have a cross section that is D-shaped. The flat part of the "D" may be positioned along inward surface 3101 of arcuate element 3100. This positioning may increase the contact length of inward surface 3101. Tubular structure 3110 may have a cross section that is circular, rectangular with rounded corners, or other suitable shape.

Tubular structure 3110 may have a cross section that is not uniform. Tubular structure 3110 may have a cross section that changes in size and/or shape along its length. As an example, an arcuate element 3100 used to reinforce a lower esophageal sphincter may have a tubular structure 3110 with a cross section that is circular on an anterior of the esophagus and oval along a posterior of the esophagus. As another example, an arcuate element 3100 used to reinforce a lower esophageal sphincter may have a tubular structure 3110 with a cross section that is oval along an anterior of the esophagus and more oval, or flattened, along a posterior of the esophagus.

Tubular structure 3110 may be at least partially made of a woven or braided material. The weave or braid may be at least partially made of one or more of metal, plastic, or other suitable material. The weave or braid may be at least partially made of one or more of nitinol, stainless steel, PEEK, polypropylene, or other suitable material.

Tubular structure 3110 may have a braid angle, braid density, filament diameter, filament size, and number of filaments selected to give a desired combination of compliance, resilience, porosity, and tubular strength that seeks to match the characteristics of a native sphincter to provide improved competency. In one embodiment, the weave or braid may have a braid angle of approximately 55 to 85 degrees. The weave or braid may have a braid density of approximately 70 to 100 crossings per inch. The filament diameter may be approximately 0.001 in. to 0.005 in. The number of filaments may be approximately 16 to 96.

Arcuate element 3100 may include a covering 3130. Covering 3130 may be coupled to tubular structure 3110. Covering 3130 may be discrete or formed integrally with tubular structure 3110. Covering 3130 may at least partially cover tubular structure 3110. Covering 3130 may be flexible and/or resilient. Covering 3130 may be made of ePTFE, silicone, urethane, or other suitable material. In one embodiment, covering 3130 may have a thickness of approximately 10 microns to 30 microns.

Covering 3130 may distribute forces of tubular structure 3110 in contact with adjacent tissue. Covering 3130 may reduce or prevent tissue erosion on the outside of the bodily passage by tubular structure 3110. Covering 3130 may discourage tissue ingrowth into tubular structure 3110. Covering 3130 may be configured to not substantially alter the lengthening properties of arcuate element 3100. Covering 3130 may have properties that are accounted for in the lengthening properties of arcuate element 3100.

Alternatively, arcuate element 3100 may have no covering. Tubular structure 3110 may be at least partially made of a woven or braided material with a weave or braid that is sufficiently dense to prevent tissue ingrowth. Tubular structure 3110 may be made of a woven or braided material with a weave or braid that has interstices that are small enough to prevent tissue ingrowth.

Tubular structure 3110 and/or covering 3130 may be coated with an agent or drug. Tubular structure 3110 and/or covering 3130 may release the agent or drug over time. The agent or drug may include an antibiotic to reduce the likelihood of infection.

Arcuate element 3100 may resiliently lengthen and shorten. Arcuate element 3100 may have an unlengthened state and, after lengthening, return to the unlengthened state.

Arcuate element 3100 may asymmetrically lengthen and shorten. Arcuate element 3100 may lengthen along a portion of tubular structure 3110 to accommodate non-centered passage of material through a bodily passage and arc interior 3105.

Tubular structure 3110 may be flexible. Tubular structure 3110 may be compliant. Tubular structure 3110 may give or flex at an area of wall 3113 where force is applied. Tubular structure 3110 may give or flex at an area of wall 3113 to accommodate non-centered passage of material through a bodily passage and arc interior 3105. Wall 3113 may give or flex into tubular structure lumen 3115. Tubular structure 3110 may be sufficiently rigid to maintain tubular structure lumen 3115.

Arcuate element 3100 occupies a volume when implanted in tissue. This volume may provide at least part of a space needed when arcuate element 3100 and arc interior 3105 expand. Tubular structure 3110 may have a cross section with a size that becomes smaller as arc interior 3105 expands. Tubular structure 3110 may flatten in a direction of expansion, such as perpendicular to longitudinal axis $3100x$, as arc interior 3105 expands. The space created by the reduction in cross section and/or flattening of tubular structure 3110 may reduce the amount of surrounding tissue moved and/or compressed when arcuate element 3100 and arc interior 3105 expand.

Arcuate element 3100 may exert little or no inward force when unlengthened. Arcuate element 3100 may exert an inward force when lengthened. Arcuate element 3100 may be configured to exert an inward force that is not so large as to significantly inhibit the sphincter from opening and/or expanding when material passes through the sphincter. Arcuate element 3100 may be configured to exert an inward force that is sufficiently large to help a sphincter at least partially close and/or return to an unexpanded size after the material has passed through the sphincter.

Arcuate element 3100 may exert an inward force that increases, remains constant, or decreases as arcuate element 3100 lengthens. Arcuate element 3100 may be configured with a desired amount of inward force, depending on how much closure assist is needed.

In one embodiment, an arcuate element 3100 used to reinforce a lower esophageal sphincter may exert an inward force at a pressure of approximately 5 mmHg to 15 mmHg. In another embodiment, an arcuate element 3100 used to reinforce an internal anal sphincter may exert an inward force at a pressure of approximately 5 mmHg to 30 mmHg.

FIGS. 8A-8D show one embodiment of a method for reinforcing a lower esophageal sphincter with arcuate element 3100.

Figure 8A:
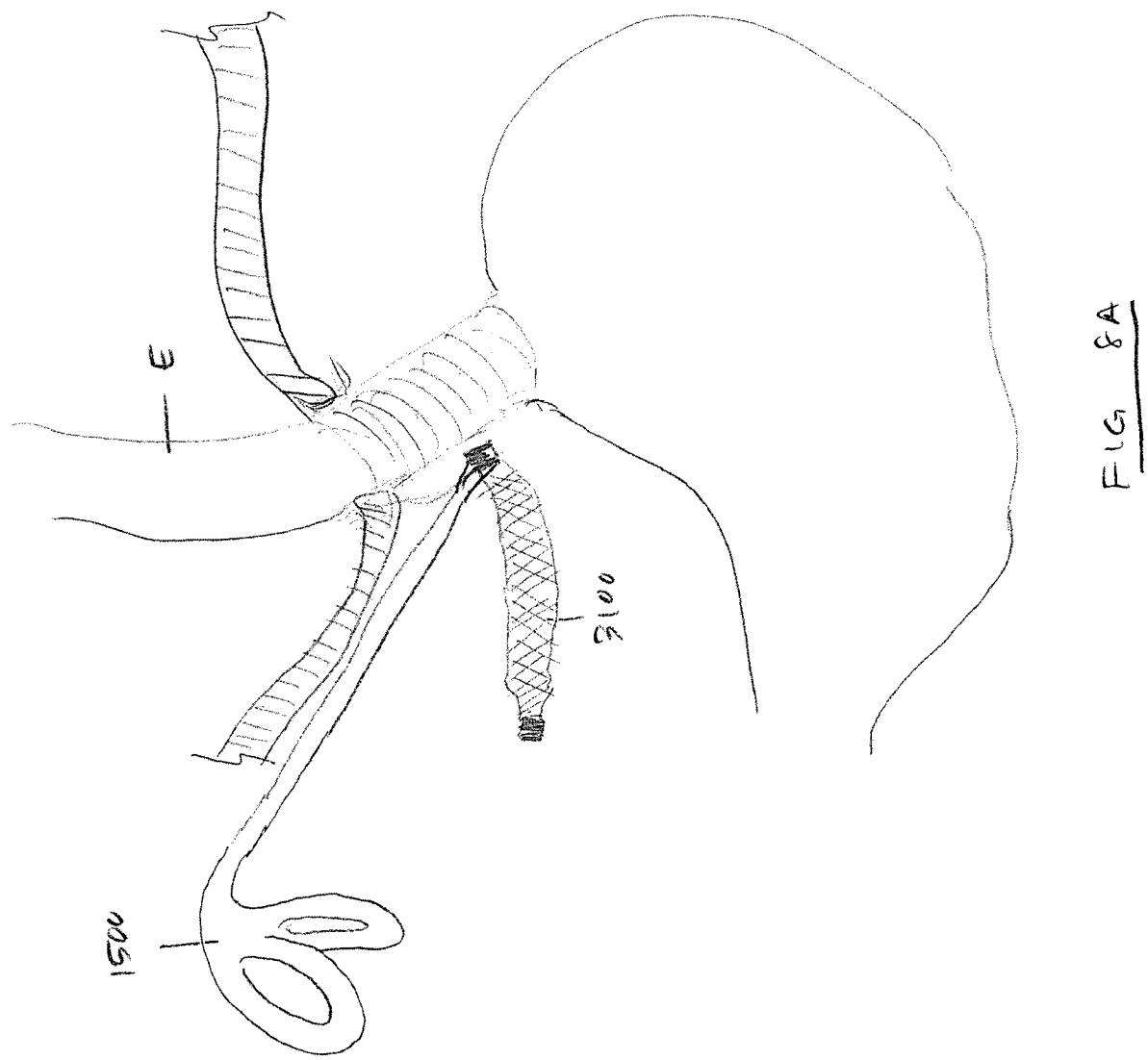
FIGS. 8A-8D show one embodiment of a method for reinforcing a lower esophageal sphincter with arcuate element 3100.

FIG. 8A shows introducing arcuate element 3100 into the abdominal cavity. The abdominal cavity may be accessed using a four-port, single-port, or other suitable laparoscopic system. A tunnel may be created at least partially around the esophagus E at the placement site. The placement site may be approximately 10 mm above to 10 mm below the lower esophageal sphincter. The tunnel may be created through surgical dissection. The posterior vagus nerve may be excluded during dissection.

Arcuate element 3100 may be available in various sizes or in a single, universal size. For arcuate element 3100 available in various sizes, a distance around an anterior of the esophagus E may be measured, and an arcuate element 3100 of suitable size may be selected based on the distance. An arcuate element 3100 of suitable inward force may also be selected based on the amount of closure assist desired.

Tubular structure 3110 may be lengthened to reduce its cross section. Tubular structure 3110 may be constrained in a reduced cross section in delivery sheath 1560 of delivery device 1500.

Delivery sheath 1560 with arcuate element 3100 may be inserted into the abdominal cavity. Delivery sheath 1560 with arcuate element 3100 may be placed in or near the tunnel created around the esophagus E. Delivery sheath 1560 may be pulled back over plunger 1570 to release arcuate element 3100 from sheath lumen 1561. Alternatively, plunger 1570 may be advanced through delivery sheath 1560 to release arcuate element 3100 from sheath lumen 1561. Tubular structure 3110 may return to an unconstrained cross section. Alternatively, arcuate element 3100 may be introduced into the abdominal cavity without delivery device 1500.

Figure 8B:
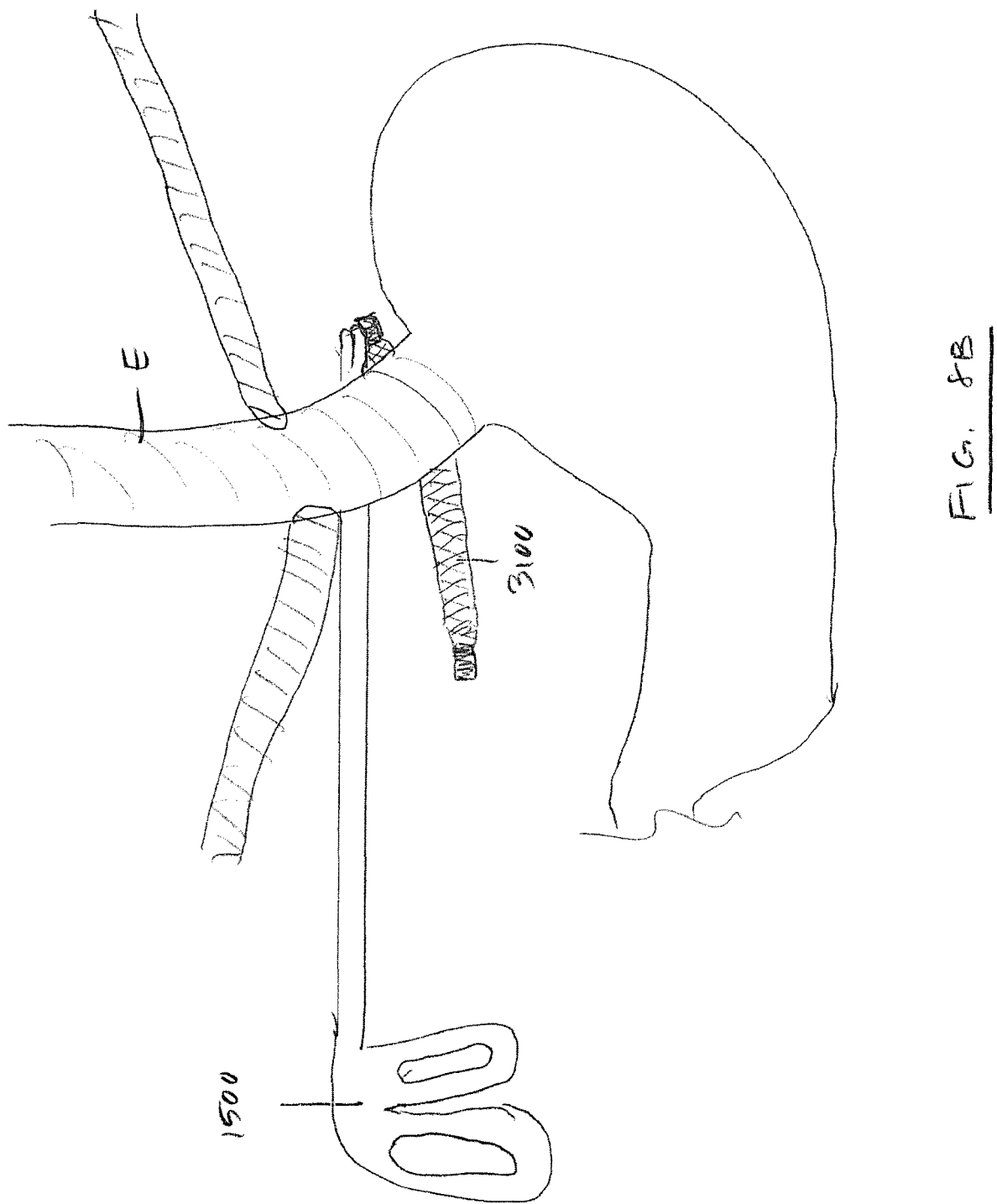

FIG. 8B shows placing arcuate element 3100 around the esophagus E. Arcuate element 3100 may be maneuvered and/or adjusted using a grasper and/or other tools.

Figure 8C:
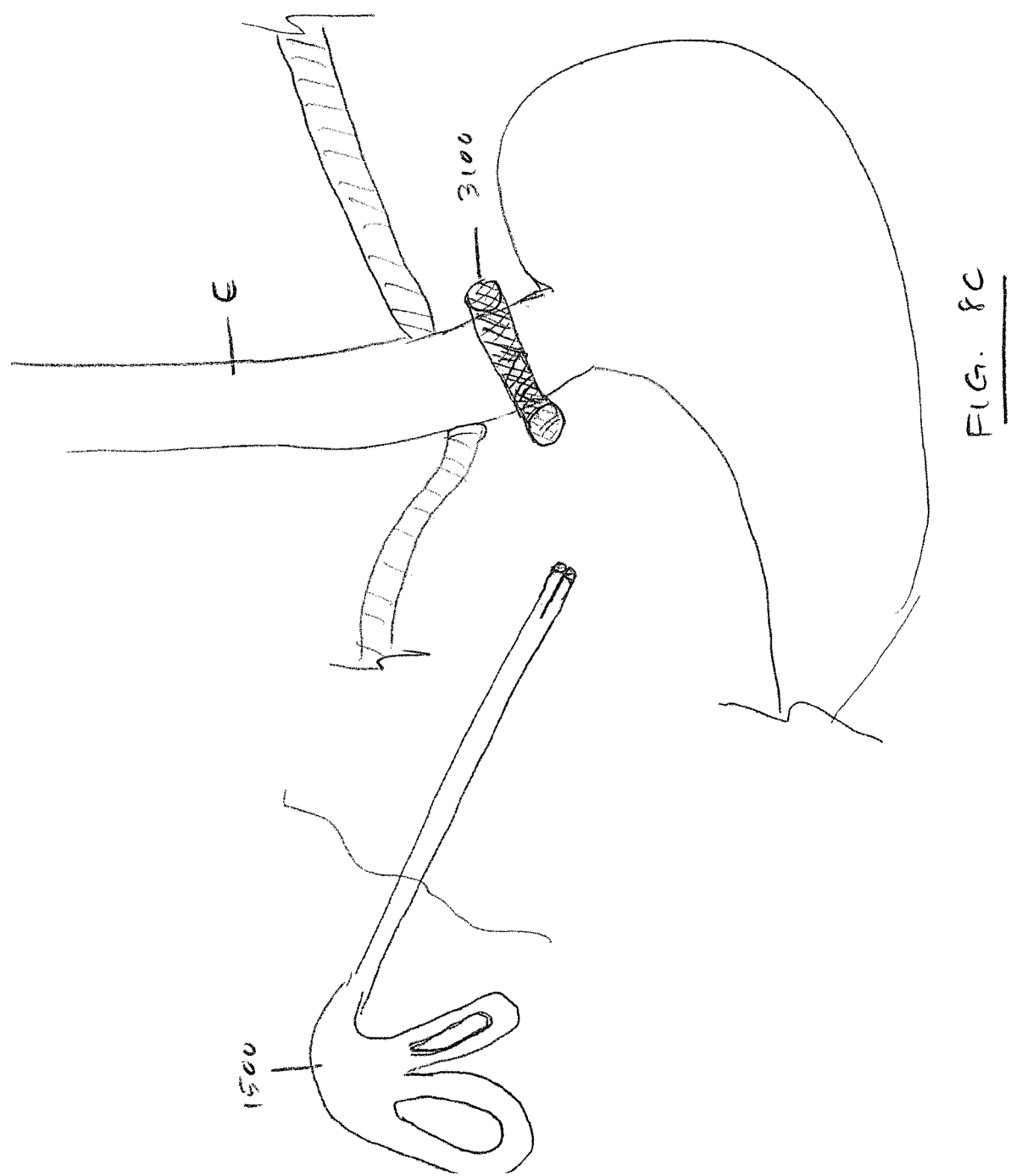
Figure 8D:
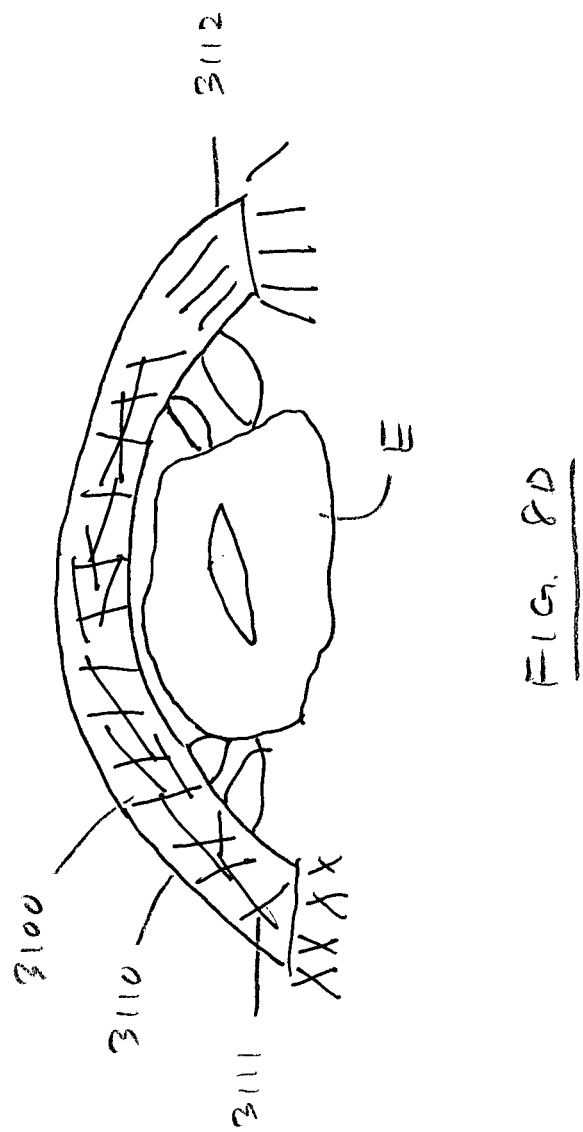

FIGS. 8C-8D show front and top views of arcuate element 3100 placed on the anterior side of the esophagus E. First end 3111 and second 3112 of tubular structure 3110 may be sutured to adjacent tissue and/or a wall of the esophagus E. Arcuate element 3100 may wrap approximately halfway around esophagus E.

Arcuate element 3100 may be removed by dissecting tissue surrounding arcuate element 3100, detaching first end 3111 and second 3112 from adjacent tissue and/or the wall of the esophagus E, and pulling on one end of tubular structure 3110 to reduce a cross section of tubular structure 3110 and remove arcuate element 3100 from around the esophagus E.

Sphincter bulking devices are described. Sphincter bulking devices may add volume and/or encourage tissue growth around a sphincter to bolster the sphincter. Sphincter bulking devices may be placed outside of and/or within a wall of a bodily passage such as an esophagus, rectum, urethra, intestine, or other bodily passage. Sphincter bulking devices may be placed at or near a sphincter, such as a lower esophageal sphincter, internal anal sphincter, urinary sphincter, pyloric sphincter, or other sphincter.

Figure 9A:
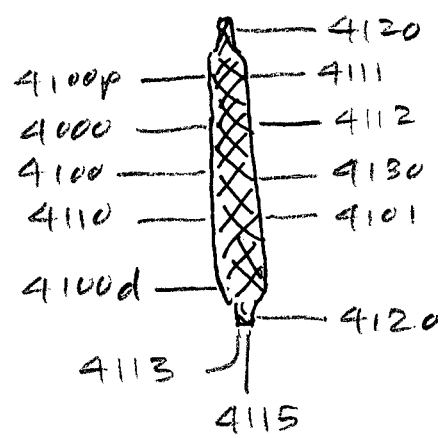
FIGS. 9A-9B show two embodiments of a sphincter bulking device 4000.
Figure 9B:
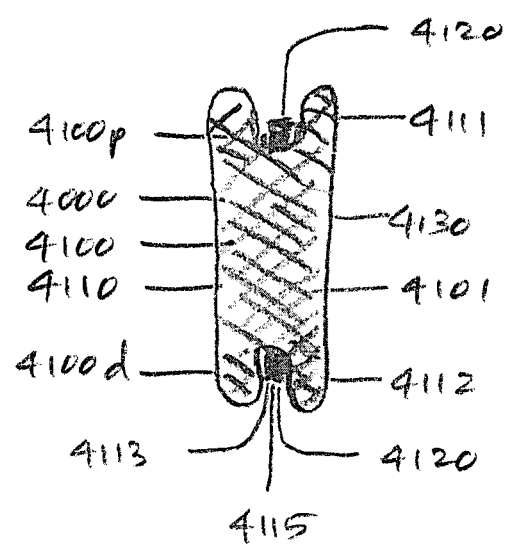

FIGS. 9A-9B show two embodiments of a sphincter bulking device 4000.

Sphincter bulking device 4000 may include at least one bulking element 4100. Bulking element 4100 may have a proximal portion 4100p and a distal portion 4100d. Bulking element 4100 may have an inward surface 4101.

One or more bulking elements 4100 may be placed on an outside of a bodily passage, such as against an outer surface of a wall of the bodily passage. One or more bulking elements 4100 may be placed within a wall of a bodily passage, between an inner surface and outer surface of the wall. For example, two to eight bulking elements 4100 may be placed between a mucosa and an outer surface of an esophagus. Bulking elements 4100 may be spaced evenly or irregularly.

In one embodiment, bulking element 4100 used to bulk up a lower esophageal sphincter may have a length of approximately 10 mm to 20 mm.

Bulking element 4100 may include a tubular structure 4110. Tubular structure 4110 may include a first end 4111, a second 4112, and a wall 4113. Tubular structure 4110 may be hollow, with wall 4113 defining a tubular structure lumen 4115.

Tubular structure 4110 may have a cross section that is oval or elliptical. The longest axis of the oval, or the major axis of the ellipse, may be oriented parallel or substantially parallel to an outside surface of the bodily passage. The shortest axis of the oval, or the minor axis of the ellipse, may be oriented perpendicular or substantially perpendicular to an outside surface of the bodily passage. This orientation of the longest axis or major axis may increase the contact length of inward surface 4101. In one embodiment, tubular structure 4110 may have a longest axis or major axis of approximately 5 mm to 10 mm, and a shortest axis or minor axis of approximately 3 mm to 5 mm.

Tubular structures 4110 of varying cross sections may be used depending on a position of bulking element 4100. As an example, bulking elements 4100 placed on an anterior of the lower esophageal sphincter may have a cross section that is circular, while bulking elements 4100 placed on a posterior of the lower esophageal sphincter may have a cross section that is oval.

Tubular structure 4110 may be at least partially made of a woven or braided material. The weave or braid may be at least partially made of one or more of metal, plastic, or other suitable material. The weave or braid may be at least partially made of one or more of nitinol, stainless steel, PEEK, polypropylene, or other suitable material.

Tubular structure 4110 may have a braid angle, braid density, filament diameter, filament size, and number of filaments selected to give a desired combination of compliance, resilience, porosity, and tubular strength that seeks to match the characteristics of a native sphincter to provide improved competency. In one embodiment, the weave or braid may have a braid angle of approximately 55 to 85 degrees. The weave or braid may have a braid density of approximately 70 to 100 crossings per inch. The filament diameter may be approximately 0.002 in. to 0.006 in. The number of filaments may be approximately 8 to 72.

Bulking element 4100 may include caps 4120. Caps 4120 may be coupled to first end 4111 and/or second end 4112 of tubular structure 4110. Caps 4120 may be atraumatic. Caps 4120 may reduce the likelihood of fraying at first end 4111 and/or second end 4112. Caps 4120 may be hollow to allow access to tubular structure lumen 4115. Caps 4120 may include one or more grasping features, such as grasping tabs and/or suture loops, which allow caps 4120 to be more easily handled by graspers. Caps 4120 may be exposed, as shown in FIG. 8A, or be hidden by at least partially inverting first end 4111 and/or second end 4112 of tubular structure 4110, as shown in FIG. 8B.

Bulking element 4100 may include a covering 4130. Covering 4130 may be coupled to tubular structure 4110. Covering 4130 may be discrete or formed integrally with tubular structure 4110. Covering 4130 may at least partially cover tubular structure 4110. Covering 4130 may be flexible and/or resilient. Covering 4130 may be made of ePTFE, silicone, urethane, or other suitable material. In one embodiment, covering 4130 may have a thickness of approximately 10 microns to 30 microns.

Covering 4130 may distribute forces of tubular structure 4110 in contact with adjacent tissue. Covering 4130 may reduce or prevent tissue erosion on the outside of the bodily passage by tubular structure 4110. Covering 4130 may discourage tissue ingrowth into tubular structure 4110.

Alternatively, bulking element 4100 may have no covering. Tubular structure 4110 may be at least partially made of a woven or braided material with a weave or braid that is sufficiently dense to prevent tissue ingrowth. Tubular structure 4110 may be made of a woven or braided material with a weave or braid that has interstices that are small enough to prevent tissue ingrowth.

Tubular structure 4110 and/or covering 4130 may be coated with an agent or drug. Tubular structure 4110 and/or covering 4130 may release the agent or drug over time. The agent or drug may include an antibiotic to reduce the likelihood of infection.

Tubular structure 4110 may be flexible. Tubular structure 4110 may be compliant. Tubular structure 4110 may give or flex at an area of wall 4113 where force is applied. Tubular structure 4110 may give or flex at an area of wall 4113 to accommodate passage of material through a bodily passage. Wall 4113 may give or flex into tubular structure lumen 4115. Tubular structure 4110 may be sufficiently rigid to maintain tubular structure lumen 4115.

Figure 10A:
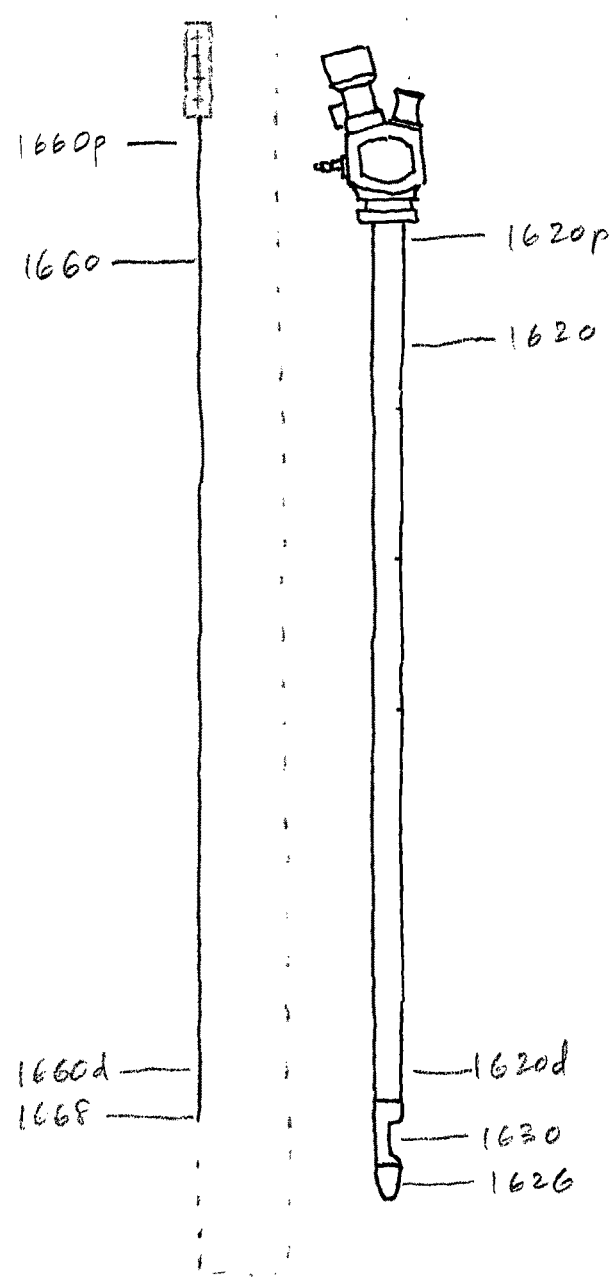
FIGS. 10A-10D show one embodiment of a delivery device 1600.
Figure 10B:
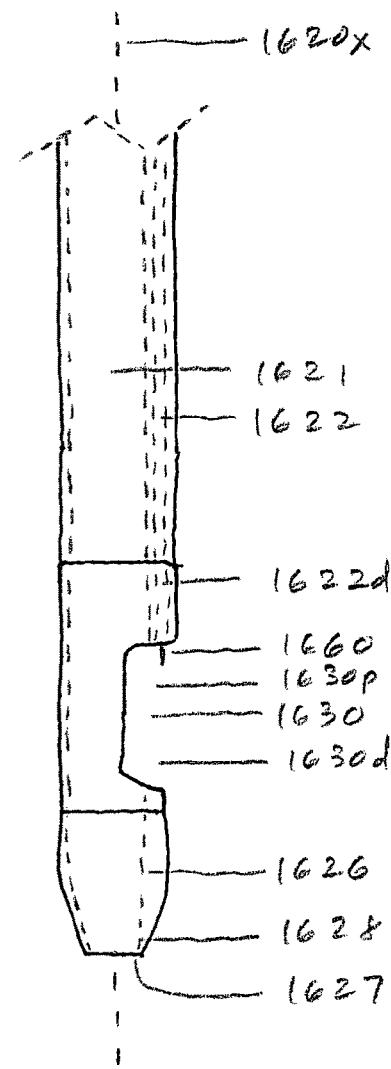
Figures 10C, 10D:
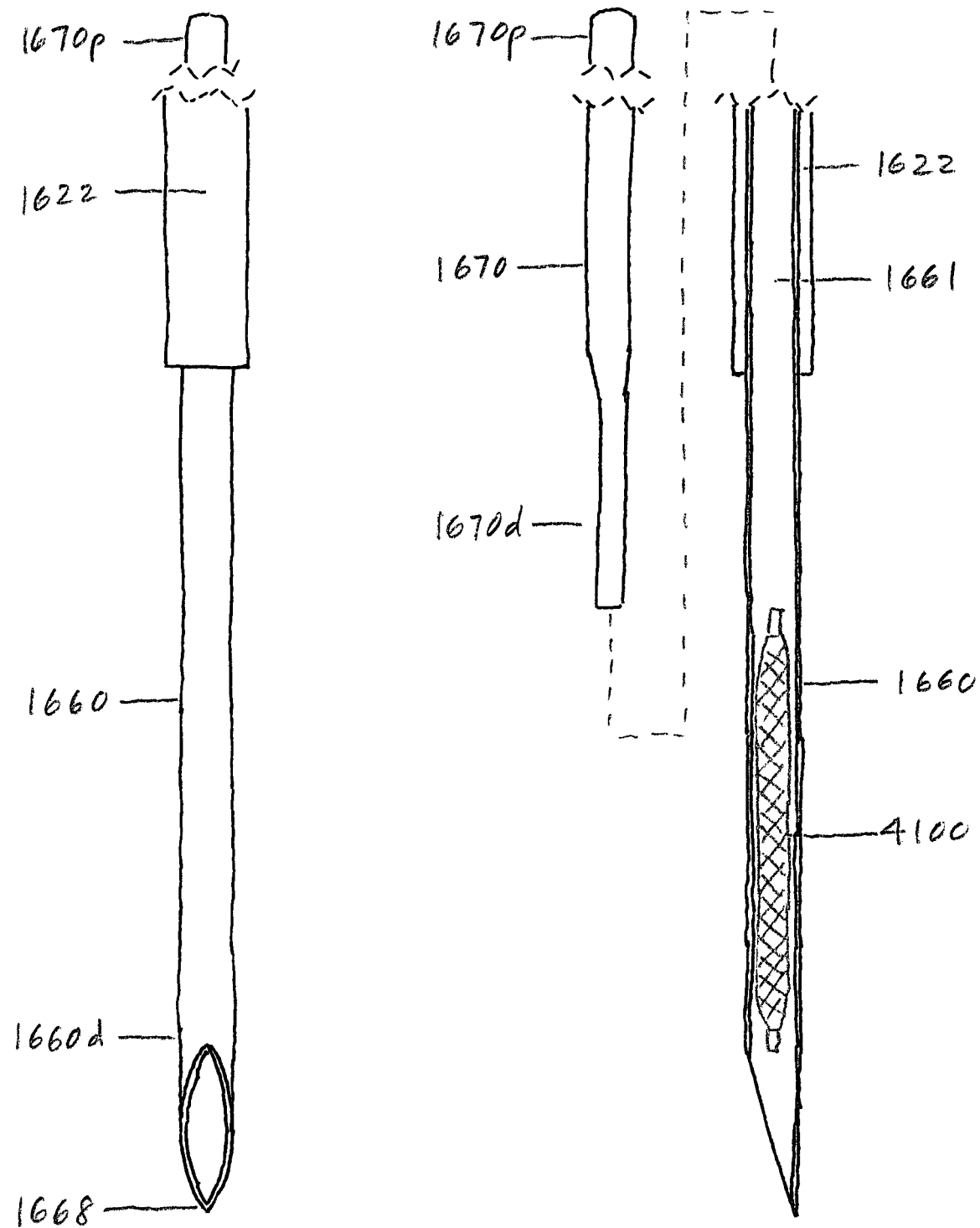

FIGS. 10A-10D show one embodiment of a delivery device 1600. FIG. 10A shows a side view of delivery device 1600. FIG. 10B shows an enlarged view of a cavity 1630 of delivery device 1600. FIG. 10C shows an enlarged view of a delivery needle 1660. FIG. 10D shows a cross-sectional view of delivery needle 1660. FIGS. 10C-10D show delivery needle 1660 loaded with a bulking element 4100. FIGS. 10C-10D show delivery needle 1660 advanced out of a secondary lumen 1622 of a catheter 1620.

Delivery device 1600 may be configured to place bulking element 4100 in and/or outside a tissue wall.

Delivery device 1600 may include a catheter 1620. Catheter 1620 may include a proximal portion 1620p, a distal portion 1620d, and a longitudinal axis 1620x.

Catheter 1620 may include a primary lumen 1621. Primary lumen 1621 may be configured to accommodate an endoscope or other instrument.

Catheter 1620 may include at least one secondary lumen 1622. Secondary lumen 1622 may be formed in a wall of catheter 1620. Secondary lumen 1622 may include a proximal portion 1622p and a distal portion 1622d. Secondary lumen 1622 may be configured to accommodate a delivery needle.

Distal portion 1622d of secondary lumen 1622 may be angled and/or curved inward toward longitudinal axis 1620x of catheter 1620. Distal portion 1622d of secondary lumen 1622 may be angled and/or curved inward toward longitudinal axis 1620x from approximately 0 degrees to 10 degrees.

Catheter 1620 may include a tip 1626. Tip 1626 may be coupled to distal portion 1620d of catheter 1620. Tip 1626 may include an opening 1627. Opening 1627 may be in communication with primary lumen 1621. Tip 1626 include a valve 1628 coupled to opening 1627. Valve 1628 may be configured to close opening 1627 when a vacuum is applied to primary lumen 1621. Valve 1628 may include a duckbill valve or any other suitable valve.

Catheter 1620 may have a width of approximately 10 mm to 20 mm.

Delivery device 1600 may include a cavity 1630 formed in catheter 1620. Cavity 1630 may be formed in a side of catheter 1620. Cavity 1630 may be circumferential and extend completely around catheter 1620. Cavity 1630 may be formed at tip 1626 of catheter 1620. Cavity 1630 may include a proximal side 1630p and a distal side 1630d. Cavity 1630 may be at or near distal portion 1620d of catheter 1620. Cavity 1630 may be in communication with primary lumen 1621 and secondary lumen 1622.

Cavity 1630 may be configured to draw in a tissue wall.

Cavity 1630 may cut completely through distal portion 1622d of secondary lumen 1622. Distal portion 1622d of secondary lumen 1622 may be positioned at a proximal side 1630p of cavity 1630.

Cavity 1630 may have a length of approximately 10 mm to 40 mm. Cavity 1630 may have a width of approximately 10 mm to 20 mm.

Delivery device 1600 may include a delivery needle 1660. Delivery needle 1660 may include a proximal portion 1660p and a distal portion 1660d. Delivery needle 1660 may be slidably disposed within secondary lumen 1622. Delivery needle 1660 may be configured to be advanced out of and withdrawn into secondary lumen 1622.

Delivery needle 1660 may include a needle lumen 1661. Needle lumen 1661 may be configured to be loaded with bulking element 4100 in a collapsed or delivery configuration. Needle lumen 1661 may also be configured to be loaded with a therapeutic agent. Therapeutic agent may include any one or any combination of a phospholipid gel, hyaluronic acid, and other agents.

Delivery needle 1660 may include a tip 1668. Tip 1668 may be coupled to distal portion 1660d of delivery needle 1660. Tip 1668 may be configured to pierce a tissue wall. Tip 1668 may be sharp.

Distal portion 1660d of delivery needle 1660 may be angled and/or curved inward toward longitudinal axis 1620x of catheter 1620. Distal portion 1660d of delivery needle 1660 may be angled and/or curved inward toward longitudinal axis 1620x from approximately 0 degrees to 10 degrees. This may reduce the likelihood of contacting bodily parts on the other side of a tissue wall.

Delivery needle 1660 may be spring-loaded, and may be configured to be advanced out of and/or withdrawn into secondary lumen 1622 quickly, such as in 100 ms or less. This may reduce tenting of the tissue wall as delivery needle 1660 is advanced through the tissue wall.

Delivery device 1600 may include a pushrod 1670. Pushrod 1670 may include a proximal portion 1670p and a distal portion 1670d. Pushrod 1670 may be slidably disposed within needle lumen 1661.

Pushrod 1670 may be configured to push bulking element 4100 out of needle lumen 1661 of delivery needle 1660.

FIGS. 11A-11E show one embodiment of a method for adding bulk to a lower esophageal sphincter with one or more bulking elements 4100.

Figure 11A:
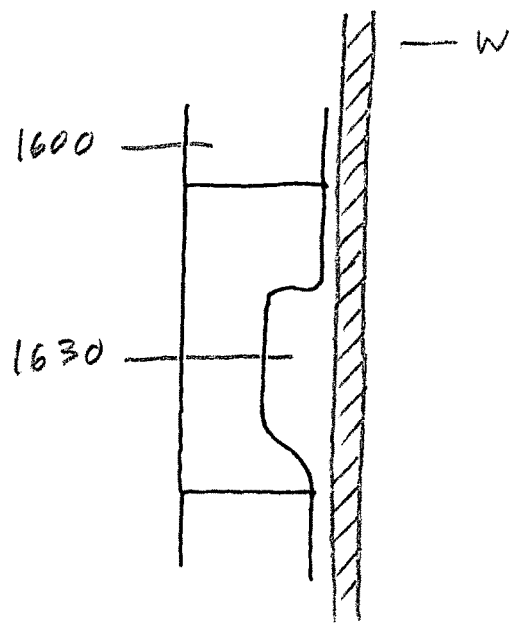
FIGS. 11A-11E show one embodiment of a method for adding bulk to a lower esophageal sphincter with bulking elements 4100.

FIG. 11A shows introducing delivery device 1600 into the esophagus E. Cavity 1630 of delivery device 1600 may be positioned next to the esophageal wall W. Tubular structure 41110 may be lengthened to reduce its cross section. Tubular structure 4110 may be constrained in a reduced cross section in delivery needle 1660 of delivery device 1600.

Figure 11B:
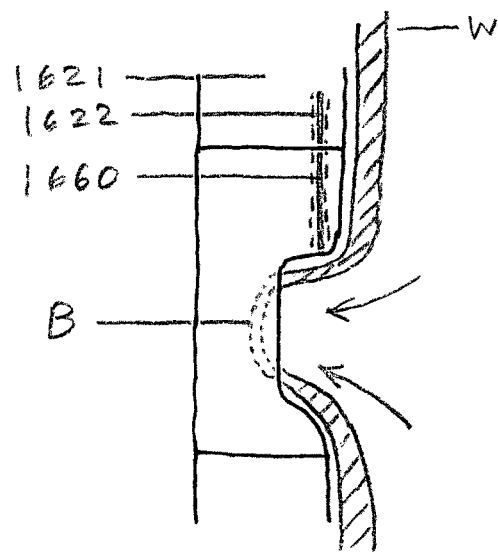

FIG. 11B shows forming a bulge B in the esophageal wall W. Delivery needle 1660 is retracted completely within secondary lumen 1622. A vacuum may be applied to cavity 1630 to draw the esophageal wall W into cavity 1630 to form the bulge B. The vacuum may be approximately 30 mmHg to 300 mmHg.

Figure 11C:
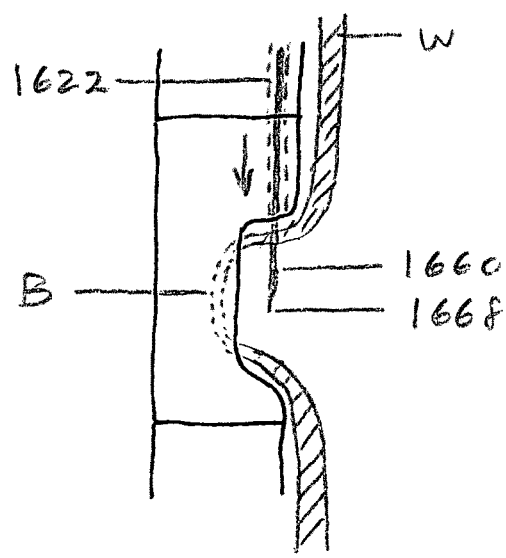

FIG. 11C shows piercing the bulge B. Delivery needle 1660 may be advanced a set distance out of secondary lumen 1622 of catheter 1620. Delivery needle 1660 may be advanced through the bulge B to position tip 1668 of delivery needle 1660 on an outside of the esophagus E. Alternatively, delivery needle 1660 may be advanced into the esophageal wall W to position tip 1668 of delivery needle 1660 within the esophageal wall W.

Figure 11D:
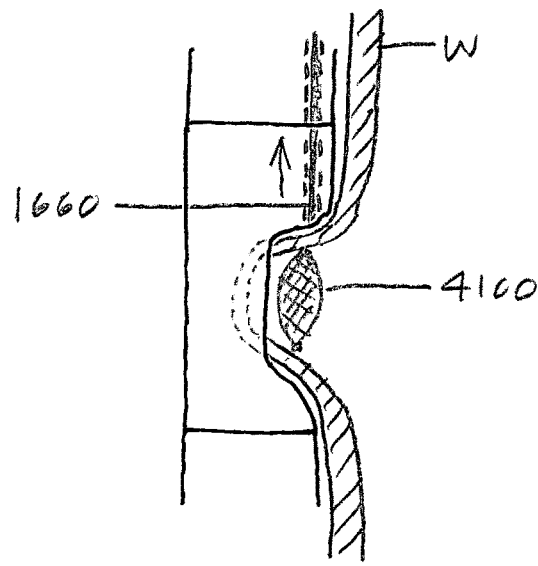

FIG. 11D shows placing bulking element 4100 on the outside of the esophagus E. Alternatively, bulking element 4100 may be placed within the esophageal wall W. Delivery needle 1660 may be pulled back over pushrod 1670 to release bulking element 4100 from needle lumen 1661. Alternatively, pushrod 1670 may be advanced a set distance through delivery needle 1660 to release bulking element 4100 from needle lumen 1661. A therapeutic agent may also be released from needle lumen 1661. Bulking element 4100 may return to an unconstrained cross section. Distal portion 4100d of bulking element 4100 may be placed at or near the gastroesophageal junction (GEJ).

Figure 11E:
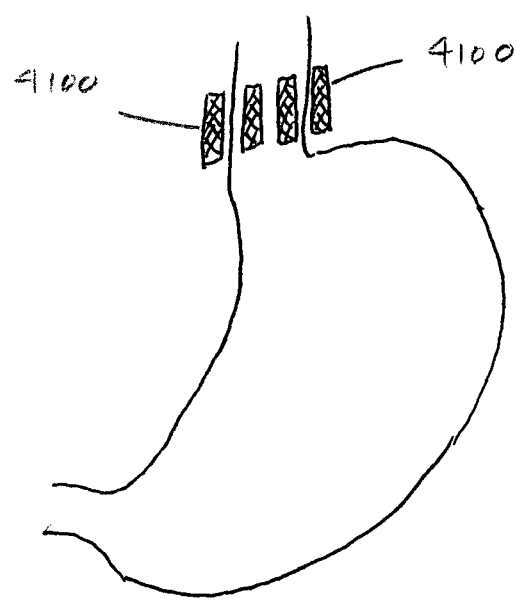

FIG. 11E shows a plurality of bulking elements 4100 placed around the lower esophageal sphincter.

While the foregoing has been with reference to particular embodiments of the invention, it will be appreciated by those skilled in the art that changes in these embodiments may be made without departing from the principles and spirit of the invention.

What is claimed is:

1. A sphincter reinforcement device comprising:
a ring including a tubular structure, the ring configured to be placed at least partially around an outside of a bodily passage, the ring being resiliently expandable, the tubular structure being hollow and having a first end and a second end, the first end configured to be coupled to the second end, the tubular structure including a braided material, the ring configured to expand to allow material to pass through the bodily passage, the ring configured to return to an unexpanded size after the material has passed through the bodily passage, the tubular structure having a cross section with a size that becomes smaller as the ring expands.

2. The device of claim 1, wherein the ring defines a ring lumen having an unexpanded size that is the same size or slightly smaller than an outside of the bodily passage.

3. The device of claim 1, wherein the tubular structure has a cross section that is oval.

4. The device of claim 3, wherein the oval has a longest axis that is parallel to a longitudinal axis of the ring.

5. The device of claim 1, wherein the tubular structure has a cross section that is not uniform.

6. The device of claim 1, wherein the ring exerts an inward force when expanded that is not so large as to inhibit material from passing through the bodily passage.

7. The device of claim 1, wherein the ring exerts an inward force when expanded that is sufficiently large to help the sphincter at least partially close after material has passed through the bodily passage.

8. The device of claim 1, further comprising:
a first connector coupled to the first end of the tubular structure, and a second connector coupled to the second end of the tubular structure, the first connector configured to detachably couple to the second connector.

9. The device of claim 1, further comprising:
a covering coupled to the tubular structure, the covering at least partially covering the tubular structure.

10. The device of claim 1, wherein the braided material is made of a metal.

11. A method for reinforcing a sphincter of a bodily passage, the method comprising:
placing a ring at least partially around an outside of the bodily passage, the ring being resiliently expandable, the ring including a tubular structure, the tubular structure being hollow and including a braided material, the ring configured to expand to allow material to pass through the bodily passage, the ring configured to return to an unexpanded size after the material has passed through the bodily passage, the tubular structure having a cross section with a size that becomes smaller as the ring expands; and
coupling a first end of the tubular structure to a second end of the tubular structure.

12. The method of claim 10, further comprising:
measuring a distance around the outside of the bodily passage; and
selecting a ring defining a ring lumen having an unexpanded size that is the same size or slightly smaller than the outside of the bodily passage.

* * * * *